(12) United States Patent
Szedlacsek et al.

(10) Patent No.: US 11,834,518 B2
(45) Date of Patent: Dec. 5, 2023

(54) INTERFERENCE PEPTIDES AS INHIBITORS OF INTERACTIONS RELATED TO AMPAR ENDOCYTOSIS

(71) Applicants: Stefan Eugen Szedlacsek, Bucharest (RO); Rodica-Aura Badea, Bucharest (RO); Horea-Stefan Szedlacsek, Bucharest (RO)

(72) Inventors: Stefan Eugen Szedlacsek, Bucharest (RO); Rodica-Aura Badea, Bucharest (RO); Horea-Stefan Szedlacsek, Bucharest (RO); Lucian Hritcu, judetul Iasi (RO)

(73) Assignees: Stefan Eugen Szedlacsek, Bucharest (RO); Rodica-Aura Badea, Bucharest (RO); Horea-Stefan Szedlacsek, Bucharest (RO)

(*) Notice: Subject to any disclaimer, the term of this patent is extended or adjusted under 35 U.S.C. 154(b) by 0 days.

(21) Appl. No.: 18/150,680

(22) Filed: Jan. 5, 2023

(65) Prior Publication Data

US 2023/0159589 A1    May 25, 2023

Related U.S. Application Data

(63) Continuation of application No. PCT/IB2021/057960, filed on Aug. 31, 2021.

(30) Foreign Application Priority Data

Aug. 31, 2020   (RO) .............................. a 2020 00548

(51) Int. Cl.
   *C07K 7/06*     (2006.01)
   *A61K 38/00*    (2006.01)

(52) U.S. Cl.
   CPC ............. *C07K 7/06* (2013.01); *A61K 38/00* (2013.01)

(58) Field of Classification Search
   CPC ................... C07K 7/06; A61K 38/00
   See application file for complete search history.

(56) References Cited

U.S. PATENT DOCUMENTS

| | | | |
|---|---|---|---|
| 2013/0231277 A1* | 9/2013 | Mohammadi | C07K 14/50 514/6.9 |
| 2016/0244777 A1* | 8/2016 | Coffin | C12N 15/8274 |
| 2019/0264232 A1* | 8/2019 | Hou | C12N 15/113 |
| 2022/0347266 A1 | 11/2022 | Wang | |

FOREIGN PATENT DOCUMENTS

| | | |
|---|---|---|
| WO | WO 2005/033311 A2 | 4/2005 |
| WO | WO 2012/037397 A2 | 3/2012 |
| WO | WO 2020/103889 A1 | 5/2020 |

OTHER PUBLICATIONS

Ahmadian Gholamreza et al. "Tyrosine Phosphorylation of GluR2 is Required for Insulin-Stimulated AMPA Receptor Endocytosis and LTD," The EMBO Journal / European Molecular Biology Organization, IRL Press, Oxford, vol. 23, No. 5, Mar. 10, 2004, pp. 1040-1050 (11 pages).

Scholz Ralf et al. "AMPA Receptor Signaling through BRAG2 and Arf6 Critical for Long-Term Synaptic Depression,"Neuron, vol. 66, No. 5, Jun. 10, 2010, pp. 768-780 (13 pages).

International Search Report and Written Opinion of International Searching Authority for International Patent Application No. PCT/IB2021/057960, dated Dec. 14, 2021 (11 pages).

* cited by examiner

*Primary Examiner* — Amber D Steele
(74) *Attorney, Agent, or Firm* — NIXON PEABODY LLP

(57) ABSTRACT

The invention relates to interference peptides as inhibitors of the interactions related to AMPA receptor endocytosis, to peptide compounds comprising said peptides that can be used in medicine, in the field of neurology and psychiatry, in particular for the prevention and therapy of mild cognitive impairment in neurodegenerative diseases or in the prophylaxis of depression and anxiety, as well as to peptidomimetic compounds of interference peptides with a blocking effect on the interaction between AMPA receptor and STEP phosphatase and to a method of inhibiting AMPA receptor endocytosis in neurons, especially in synaptic neurons.

3 Claims, 25 Drawing Sheets

Specification includes a Sequence Listing.

SEQUENCE LISTING

```
Sequence total quantity: 79
SEQ ID NO: 1            moltype = AA  length = 6
FEATURE                 Location/Qualifiers
source                  1..6
                        mol_type = protein
                        organism = synthetic construct
                        note = Interference peptide capable of inhibiting the
                          formation/disrupting the STEP-GluA2 complex or the
                          GluA2-BRAG2 complex
SITE                    6
                        note = Phosphorylation - Phosphorylation of the tyrosine in
                          position 6
SEQUENCE: 1
EGYNVY                                                                          6

SEQ ID NO: 2            moltype = AA  length = 7
FEATURE                 Location/Qualifiers
source                  1..7
                        mol_type = protein
                        organism = synthetic construct
                        note = Interference peptide capable of inhibiting the
                          formation/disrupting the STEP-GluA2 complex or the
                          GluA2-BRAG2 complex
SITE                    6
                        note = Phosphorylation - Phosphorylation of the tyrosine in
                          position 6
SEQUENCE: 2
EGYNVYE                                                                         7

SEQ ID NO: 3            moltype = AA  length = 8
FEATURE                 Location/Qualifiers
source                  1..8
                        mol_type = protein
                        organism = synthetic construct
                        note = Interference peptide capable of inhibiting the
                          formation/disrupting the STEP-GluA2 complex or the
                          GluA2-BRAG2 complex
SITE                    6
                        note = Phosphorylation - Phosphorylation of the tyrosine in
                          position 6
SEQUENCE: 3
EGYNVYGD                                                                        8

SEQ ID NO: 4            moltype = AA  length = 6
FEATURE                 Location/Qualifiers
source                  1..6
                        mol_type = protein
```

```
                              -continued organism = synthetic construct
                         note = Interference peptide capable of inhibiting the
                            formation/disrupting the STEP-GluA2 complex or the
                            GluA2-BRAG2 complex
SEQUENCE: 4
EGYNVY                                                                        6

SEQ ID NO: 5             moltype = AA  length = 7
FEATURE                  Location/Qualifiers
source                   1..7
                         mol_type = protein
                         organism = synthetic construct
                         note = Interference peptide capable of inhibiting the
                            formation/disrupting the STEP-GluA2 complex or the
                            GluA2-BRAG2 complex
SEQUENCE: 5
EGYNVYE                                                                       7

SEQ ID NO: 6             moltype = AA  length = 8
FEATURE                  Location/Qualifiers
source                   1..8
                         mol_type = protein
                         organism = synthetic construct
                         note = Interference peptide capable of inhibiting the
                            formation/disrupting the STEP-GluA2 complex or the
                            GluA2-BRAG2 complex
SEQUENCE: 6
EGYNVYGD                                                                      8

SEQ ID NO: 7             moltype = AA  length = 284
FEATURE                  Location/Qualifiers
source                   1..284
                         mol_type = protein
                         organism = Homo sapiens
SEQUENCE: 7
SMSRVLQAEE LHEKALDPFL LQAEFFEIPM NFVDPKEYDI PGLVRKNRYK TILPNPHSRV    60
CLTSPDPDDP LSSYINANYI RGYGGEEKVY IATQGPIVST VADFWRMVWQ EHTPIIVMIT   120
NIEEMNEKCT EYWPEEQVAY DGVEITVQKV IHTEDYRLRL ISLKSGTEER GLKHYWFTSW   180
PDQKTPDRAP PLLHLVREVE EAAQQEGPHC APIIVHSSAG IGRTGCFIAT SICCQQLRQE   240
GVVDILKTTC QLRQDRGGMI QTCEQYQFVH HVMSLYEKQL SHQS                    284

SEQ ID NO: 8             moltype = AA  length = 383
FEATURE                  Location/Qualifiers
source                   1..383
                         mol_type = protein
                         organism = Homo sapiens
SEQUENCE: 8
GAMGSGIPMS WDSPAFSNDV IRKRHYRIGL NLFNKKPEKG VQYLIERGFV PDTPVGAHF     60
LLQRKGLSRQ MIGEFLGNRQ KQFNRDVLDC VVDEMDFSTM ELDEALRKFQ AHIRVQGKAQ   120
KVERLIEAFS QRYCICNPGV VRQFRNPDTI FILAFAIILL NTDMYSPNVK PERKMKLEDF   180
IKNLRGVDDG EDIPREMLMG IYERIRKREL KTNEDHVSQV QKVEKLIVGK KPIGSLHPGL   240
GCVLSLPHRR LVCYCRLFEV PDPNKPQKLG LHQREIFLFN DLLVVTKIFQ KKKNSVTYSF   300
RQSFSLYGMQ VLLFENQYYP NGIRLTSSVP GADIKVLINF NAPNPQDRKK FTDDLRESIA   360
EVQEMEKHRI ESELEKQKGV VRP                                           383

SEQ ID NO: 9             moltype = AA  length = 8
FEATURE                  Location/Qualifiers
source                   1..8
                         mol_type = protein
                         organism = synthetic construct
VARIANT                  6
                         note = Tyrosine or phosphorylated tyrosine
VARIANT                  7
                         note = E, G or absent
VARIANT                  8
                         note = This residue is D when position 7 is G, and absent
                            when position 7 is E
SEQUENCE: 9
EGYNVXXX                                                                      8

SEQ ID NO: 10            moltype = AA  length = 5
FEATURE                  Location/Qualifiers
source                   1..5
                         mol_type = protein
                         organism = synthetic construct
SITE                     5
                         note = phosphorylated tyrosine
SEQUENCE: 10
GYNVY                                                                         5
```

```
SEQ ID NO: 11            moltype = AA   length = 9
FEATURE                  Location/Qualifiers
source                   1..9
                         mol_type = protein
                         organism = synthetic construct
SEQUENCE: 11
YKEGYNVYG                                                              9

SEQ ID NO: 12            moltype = AA   length = 51
FEATURE                  Location/Qualifiers
source                   1..51
                         mol_type = protein
                         organism = synthetic construct
SEQUENCE: 12
IEFCYKSRAE AKRMKVAKNA QNINPSSSQN SQNFATYKEG YNVYGIESVK I               51

SEQ ID NO: 13            moltype = AA   length = 4
FEATURE                  Location/Qualifiers
source                   1..4
                         mol_type = protein
                         organism = synthetic construct
SEQUENCE: 13
NVYG                                                                   4

SEQ ID NO: 14            moltype = AA   length = 10
FEATURE                  Location/Qualifiers
source                   1..10
                         mol_type = protein
                         organism = unidentified
VARIANT                  1
                         note = I or V
VARIANT                  4
                         note = Any amino acid
VARIANT                  7
                         note = Any amino acid
VARIANT                  10
                         note = S or T
SEQUENCE: 14
XHCXAGXGRX                                                             10

SEQ ID NO: 15            moltype = AA   length = 11
FEATURE                  Location/Qualifiers
source                   1..11
                         mol_type = protein
                         organism = synthetic construct
SITE                     10
                         note = phosphorylated tyrosine
SEQUENCE: 15
ATYKEGYNVY G                                                           11

SEQ ID NO: 16            moltype = AA   length = 11
FEATURE                  Location/Qualifiers
source                   1..11
                         mol_type = protein
                         organism = synthetic construct
SITE                     10
                         note = phosphorylated tyrosine
SEQUENCE: 16
AAYKEGYNVY G                                                           11

SEQ ID NO: 17            moltype = AA   length = 11
FEATURE                  Location/Qualifiers
source                   1..11
                         mol_type = protein
                         organism = synthetic construct
SITE                     10
                         note = phosphorylated tyrosine
SEQUENCE: 17
ATAKEGYNVY G                                                           11

SEQ ID NO: 18            moltype = AA   length = 11
FEATURE                  Location/Qualifiers
source                   1..11
                         mol_type = protein
                         organism = synthetic construct
SITE                     10
                         note = phosphorylated tyrosine
SEQUENCE: 18
```

ATYAEGYNVY G                                                                      11

SEQ ID NO: 19           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 19
ATYKAGYNVY G                                                                      11

SEQ ID NO: 20           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 20
ATYKEAYNVY G                                                                      11

SEQ ID NO: 21           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 21
ATYKEGANVY G                                                                      11

SEQ ID NO: 22           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 22
ATYKEGYAVY G                                                                      11

SEQ ID NO: 23           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 23
ATYKEGYNAY G                                                                      11

SEQ ID NO: 24           moltype = AA   length = 11
FEATURE                 Location/Qualifiers
source                  1..11
                        mol_type = protein
                        organism = synthetic construct
SITE                    10
                        note = phosphorylated tyrosine
SEQUENCE: 24
ATYKEGYNVY A                                                                      11

SEQ ID NO: 25           moltype = AA   length = 10
FEATURE                 Location/Qualifiers
source                  1..10
                        mol_type = protein
                        organism = synthetic construct
SITE                    9
                        note = phosphorylated tyrosine
SEQUENCE: 25
TYKEGYNVYG                                                                        10

SEQ ID NO: 26           moltype = AA   length = 10
FEATURE                 Location/Qualifiers
source                  1..10
                        mol_type = protein
                        organism = synthetic construct
SITE                    10
                        note = phosphorylated tyrosine

```
SEQUENCE: 26
ATYKEGYNVY                                                          10

SEQ ID NO: 27           moltype = AA   length = 9
FEATURE                 Location/Qualifiers
source                  1..9
                        mol_type = protein
                        organism = synthetic construct
SITE                    8
                        note = phosphorylated tyrosine
SEQUENCE: 27
YKEGYNVYG                                                           9

SEQ ID NO: 28           moltype = AA   length = 9
FEATURE                 Location/Qualifiers
source                  1..9
                        mol_type = protein
                        organism = synthetic construct
SITE                    9
                        note = phosphorylated tyrosine
SEQUENCE: 28
TYKEGYNVY                                                           9

SEQ ID NO: 29           moltype = AA   length = 8
FEATURE                 Location/Qualifiers
source                  1..8
                        mol_type = protein
                        organism = synthetic construct
SITE                    7
                        note = phosphorylated tyrosine
SEQUENCE: 29
KEGYNVYG                                                            8

SEQ ID NO: 30           moltype = AA   length = 8
FEATURE                 Location/Qualifiers
source                  1..8
                        mol_type = protein
                        organism = synthetic construct
SITE                    8
                        note = phosphorylated tyrosine
SEQUENCE: 30
YKEGYNVY                                                            8

SEQ ID NO: 31           moltype = AA   length = 7
FEATURE                 Location/Qualifiers
source                  1..7
                        mol_type = protein
                        organism = synthetic construct
SITE                    6
                        note = phosphorylated tyrosine
SEQUENCE: 31
EGYNVYG                                                             7

SEQ ID NO: 32           moltype = AA   length = 7
FEATURE                 Location/Qualifiers
source                  1..7
                        mol_type = protein
                        organism = synthetic construct
SITE                    7
                        note = phosphorylated tyrosine
SEQUENCE: 32
KEGYNVY                                                             7

SEQ ID NO: 33           moltype = AA   length = 6
FEATURE                 Location/Qualifiers
source                  1..6
                        mol_type = protein
                        organism = synthetic construct
SITE                    5
                        note = phosphorylated tyrosine
SEQUENCE: 33
GYNVYG                                                              6

SEQ ID NO: 34           moltype = AA   length = 5
FEATURE                 Location/Qualifiers
source                  1..5
                        mol_type = protein
                        organism = synthetic construct
SITE                    4
```

```
                                note = phosphorylated tyrosine
SEQUENCE: 34
YNVYG                                                                            5

SEQ ID NO: 35           moltype = AA   length = 4
FEATURE                 Location/Qualifiers
source                  1..4
                        mol_type = protein
                        organism = synthetic construct
SITE                    3
                        note = phosphorylated tyrosine
SEQUENCE: 35
NVYG                                                                             4

SEQ ID NO: 36           moltype = AA   length = 4
FEATURE                 Location/Qualifiers
source                  1..4
                        mol_type = protein
                        organism = synthetic construct
SITE                    4
                        note = phosphorylated tyrosine
SEQUENCE: 36
YNVY                                                                             4

SEQ ID NO: 37           moltype = AA   length = 4
FEATURE                 Location/Qualifiers
source                  1..4
                        mol_type = protein
                        organism = synthetic construct
SITE                    4
                        note = phosphorylated tyrosine
SEQUENCE: 37
YNRY                                                                             4

SEQ ID NO: 38           moltype = AA   length = 7
FEATURE                 Location/Qualifiers
source                  1..7
                        mol_type = protein
                        organism = synthetic construct
SITE                    6
                        note = phosphorylated tyrosine
SEQUENCE: 38
FGYNDYG                                                                          7

SEQ ID NO: 39           moltype = AA   length = 4
FEATURE                 Location/Qualifiers
source                  1..4
                        mol_type = protein
                        organism = synthetic construct
SITE                    4
                        note = phosphorylated tyrosine
SEQUENCE: 39
YNKY                                                                             4

SEQ ID NO: 40           moltype = AA   length = 7
FEATURE                 Location/Qualifiers
source                  1..7
                        mol_type = protein
                        organism = synthetic construct
SITE                    6
                        note = phosphorylated tyrosine
SEQUENCE: 40
EKYNDYG                                                                          7

SEQ ID NO: 41           moltype = AA   length = 4
FEATURE                 Location/Qualifiers
source                  1..4
                        mol_type = protein
                        organism = synthetic construct
SITE                    3
                        note = phosphorylated tyrosine
SEQUENCE: 41
NTYG                                                                             4

SEQ ID NO: 42           moltype = AA   length = 7
FEATURE                 Location/Qualifiers
source                  1..7
                        mol_type = protein
                        organism = synthetic construct
```

```
SITE                        6
                            note = phosphorylated tyrosine
SEQUENCE: 42
FKYNDYG                                                                 7

SEQ ID NO: 43               moltype = AA   length = 4
FEATURE                     Location/Qualifiers
source                      1..4
                            mol_type = protein
                            organism = synthetic construct
SITE                        3
                            note = phosphorylated tyrosine
SEQUENCE: 43
NSYG                                                                    4

SEQ ID NO: 44               moltype = AA   length = 7
FEATURE                     Location/Qualifiers
source                      1..7
                            mol_type = protein
                            organism = synthetic construct
SITE                        6
                            note = phosphorylated tyrosine
SEQUENCE: 44
EKYNVYG                                                                 7

SEQ ID NO: 45               moltype = AA   length = 6
FEATURE                     Location/Qualifiers
source                      1..6
                            mol_type = protein
                            organism = synthetic construct
SITE                        5
                            note = phosphorylated tyrosine
SEQUENCE: 45
GYNVYR                                                                  6

SEQ ID NO: 46               moltype = AA   length = 7
FEATURE                     Location/Qualifiers
source                      1..7
                            mol_type = protein
                            organism = synthetic construct
SITE                        6
                            note = phosphorylated tyrosine
SEQUENCE: 46
FGYNVYG                                                                 7

SEQ ID NO: 47               moltype = AA   length = 6
FEATURE                     Location/Qualifiers
source                      1..6
                            mol_type = protein
                            organism = synthetic construct
SITE                        5
                            note = phosphorylated tyrosine
SEQUENCE: 47
GYNVYK                                                                  6

SEQ ID NO: 48               moltype = AA   length = 7
FEATURE                     Location/Qualifiers
source                      1..7
                            mol_type = protein
                            organism = synthetic construct
SITE                        6
                            note = phosphorylated tyrosine
SEQUENCE: 48
FKYNVYG                                                                 7

SEQ ID NO: 49               moltype = AA   length = 4
FEATURE                     Location/Qualifiers
source                      1..4
                            mol_type = protein
                            organism = synthetic construct
SITE                        3
                            note = phosphorylated tyrosine
SEQUENCE: 49
YVYG                                                                    4

SEQ ID NO: 50               moltype = AA   length = 4
FEATURE                     Location/Qualifiers
source                      1..4
                            mol_type = protein
```

```
                              organism = synthetic construct
SITE                          3
                              note = phosphorylated tyrosine
SEQUENCE: 50
FTYG                                                                    4

SEQ ID NO: 51                 moltype = AA   length = 4
FEATURE                       Location/Qualifiers
source                        1..4
                              mol_type = protein
                              organism = synthetic construct
SITE                          3
                              note = phosphorylated tyrosine
SEQUENCE: 51
KVYG                                                                    4

SEQ ID NO: 52                 moltype = AA   length = 4
FEATURE                       Location/Qualifiers
source                        1..4
                              mol_type = protein
                              organism = synthetic construct
SITE                          3
                              note = phosphorylated tyrosine
SEQUENCE: 52
FSYG                                                                    4

SEQ ID NO: 53                 moltype = AA   length = 4
FEATURE                       Location/Qualifiers
source                        1..4
                              mol_type = protein
                              organism = synthetic construct
SITE                          3
                              note = phosphorylated tyrosine
SEQUENCE: 53
FVYG                                                                    4

SEQ ID NO: 54                 moltype = AA   length = 4
FEATURE                       Location/Qualifiers
source                        1..4
                              mol_type = protein
                              organism = synthetic construct
SITE                          3
                              note = phosphorylated tyrosine
SEQUENCE: 54
WTYG                                                                    4

SEQ ID NO: 55                 moltype = AA   length = 7
FEATURE                       Location/Qualifiers
source                        1..7
                              mol_type = protein
                              organism = synthetic construct
SITE                          6
                              note = phosphorylated tyrosine
SEQUENCE: 55
KGYNVYG                                                                 7

SEQ ID NO: 56                 moltype = AA   length = 4
FEATURE                       Location/Qualifiers
source                        1..4
                              mol_type = protein
                              organism = synthetic construct
SITE                          3
                              note = phosphorylated tyrosine
SEQUENCE: 56
WSYG                                                                    4

SEQ ID NO: 57                 moltype = AA   length = 7
FEATURE                       Location/Qualifiers
source                        1..7
                              mol_type = protein
                              organism = synthetic construct
SITE                          6
                              note = phosphorylated tyrosine
SEQUENCE: 57
KGYDVYG                                                                 7

SEQ ID NO: 58                 moltype = AA   length = 4
FEATURE                       Location/Qualifiers
source                        1..4
```

```
                          mol_type = protein
                          organism = synthetic construct
SITE                      3
                          note = phosphorylated tyrosine
SEQUENCE: 58
YTYG                                                                          4

SEQ ID NO: 59             moltype = AA   length = 6
FEATURE                   Location/Qualifiers
source                    1..6
                          mol_type = protein
                          organism = synthetic construct
SITE                      5
                          note = phosphorylated tyrosine
SEQUENCE: 59
GYDVYG                                                                        6

SEQ ID NO: 60             moltype = AA   length = 4
FEATURE                   Location/Qualifiers
source                    1..4
                          mol_type = protein
                          organism = synthetic construct
SITE                      3
                          note = phosphorylated tyrosine
SEQUENCE: 60
YSYG                                                                          4

SEQ ID NO: 61             moltype = AA   length = 7
FEATURE                   Location/Qualifiers
source                    1..7
                          mol_type = protein
                          organism = synthetic construct
SITE                      6
                          note = phosphorylated tyrosine
SEQUENCE: 61
EGYNDYG                                                                       7

SEQ ID NO: 62             moltype = AA   length = 4
FEATURE                   Location/Qualifiers
source                    1..4
                          mol_type = protein
                          organism = synthetic construct
SITE                      1
                          note = Polyethyene glycol (PEG2) spacer
SITE                      3
                          note = phosphorylated tyrosine
SEQUENCE: 62
NVYG                                                                          4

SEQ ID NO: 63             moltype = AA   length = 5
FEATURE                   Location/Qualifiers
source                    1..5
                          mol_type = protein
                          organism = synthetic construct
SITE                      1
                          note = Polyethyene glycol (PEG2) spacer
SITE                      4
                          note = phosphorylated tyrosine
SEQUENCE: 63
YNVYG                                                                         5

SEQ ID NO: 64             moltype = AA   length = 6
FEATURE                   Location/Qualifiers
source                    1..6
                          mol_type = protein
                          organism = synthetic construct
SITE                      1
                          note = Polyethyene glycol (PEG2) spacer
SITE                      6
                          note = phosphorylated tyrosine
SEQUENCE: 64
EGYNVY                                                                        6

SEQ ID NO: 65             moltype = AA   length = 4
FEATURE                   Location/Qualifiers
source                    1..4
                          mol_type = protein
                          organism = synthetic construct
SITE                      1
```

```
                              note = Polyethyene glycol (PEG2) spacer
SITE                          3
                              note = phosphorylated tyrosine
SEQUENCE: 65
NSYG                                                                         4

SEQ ID NO: 66                 moltype = AA   length = 4
FEATURE                       Location/Qualifiers
source                        1..4
                              mol_type = protein
                              organism = synthetic construct
SITE                          1
                              note = Polyethyene glycol (PEG2) spacer
SITE                          3
                              note = phosphorylated tyrosine
SEQUENCE: 66
YVYG                                                                         4

SEQ ID NO: 67                 moltype = AA   length = 7
FEATURE                       Location/Qualifiers
source                        1..7
                              mol_type = protein
                              organism = synthetic construct
SITE                          1
                              note = Polyethyene glycol (PEG2) spacer
SITE                          6
                              note = phosphorylated tyrosine
SEQUENCE: 67
FGYNVYG                                                                      7

SEQ ID NO: 68                 moltype = AA   length = 4
FEATURE                       Location/Qualifiers
source                        1..4
                              mol_type = protein
                              organism = synthetic construct
SITE                          1
                              note = Polyethyene glycol (PEG2) spacer
SITE                          3
                              note = phosphorylated tyrosine
SEQUENCE: 68
FSYG                                                                         4

SEQ ID NO: 69                 moltype = AA   length = 11
FEATURE                       Location/Qualifiers
source                        1..11
                              mol_type = protein
                              organism = synthetic construct
SITE                          10
                              note = 4-(phosphonodifluoromethyl) phenylalanine
SEQUENCE: 69
ATYKEGYNVX G                                                                11

SEQ ID NO: 70                 moltype = AA   length = 6
FEATURE                       Location/Qualifiers
source                        1..6
                              mol_type = protein
                              organism = synthetic construct
SITE                          6
                              note = 4-(phosphonodifluoromethyl) phenylalanine
SEQUENCE: 70
EGYNVF                                                                       6

SEQ ID NO: 71                 moltype = AA   length = 6
FEATURE                       Location/Qualifiers
source                        1..6
                              mol_type = protein
                              organism = synthetic construct
SITE                          6
                              note = phosphorylated tyrosine
SEQUENCE: 71
DGYNVY                                                                       6

SEQ ID NO: 72                 moltype = AA   length = 6
FEATURE                       Location/Qualifiers
source                        1..6
                              mol_type = protein
                              organism = synthetic construct
SITE                          6
                              note = phosphorylated tyrosine
```

```
SEQUENCE: 72
NGYNVY                                                                          6

SEQ ID NO: 73          moltype = AA  length = 11
FEATURE                Location/Qualifiers
source                 1..11
                       mol_type = protein
                       organism = synthetic construct
SEQUENCE: 73
ATYKEGYNVY G                                                                   11

SEQ ID NO: 74          moltype = AA  length = 7
FEATURE                Location/Qualifiers
source                 1..7
                       mol_type = protein
                       organism = synthetic construct
SITE                   6
                       note = 4-(phosphonodifluoromethyl) phenylalanine
SEQUENCE: 74
EGYNVFE                                                                         7

SEQ ID NO: 75          moltype = AA  length = 12
FEATURE                Location/Qualifiers
source                 1..12
                       mol_type = protein
                       organism = Human immunodeficiency virus 1
SEQUENCE: 75
GRKKRRQRRR PQ                                                                  12

SEQ ID NO: 76          moltype = AA  length = 6
FEATURE                Location/Qualifiers
source                 1..6
                       mol_type = protein
                       organism = synthetic construct
SEQUENCE: 76
HHHHHH                                                                          6

SEQ ID NO: 77          moltype = AA  length = 7
FEATURE                Location/Qualifiers
source                 1..7
                       mol_type = protein
                       organism = synthetic construct
VARIANT                6
                       note = Phosphorylated tyrosine, tyrosine, or
                        4-(phosphonodifluoromethyl) -L-phenylalanine (F2Pmp)
SEQUENCE: 77
EGYNVXE                                                                         7

SEQ ID NO: 78          moltype = AA  length = 11
FEATURE                Location/Qualifiers
source                 1..11
                       mol_type = protein
                       organism = Human immunodeficiency virus 1
SEQUENCE: 78
YGRKKRRQRR R                                                                   11

SEQ ID NO: 79          moltype = AA  length = 15
FEATURE                Location/Qualifiers
source                 1..15
                       mol_type = protein
                       organism = synthetic construct
SITE                   1
                       note = tetramethylrhodamine
SITE                   13
                       note = 4-(phosphonodifluoromethyl) phenylalanine
SEQUENCE: 79
NFATYKEGYN VFGIE                                                               15
```

INTERFERENCE PEPTIDES AS INHIBITORS OF INTERACTIONS RELATED TO AMPAR ENDOCYTOSIS

CROSS-REFERENCE TO RELATED APPLICATIONS

This application is a bypass continuation of International Application No. PCT/M2021/057960, filed Aug. 31, 2021, which claims the benefit of, and priority to, Romanian Patent Application Serial No. a 2020 00548, filed on Aug. 31, 2020, each of which is hereby incorporated by reference herein in its entirety.

SEQUENCE LISTING

The instant application contains a Sequence Listing which has been submitted electronically in XML file format and is hereby incorporated by reference in its entirety. Said XML copy, created on Nov. 17, 2022, is named 098071-000002USPX_SL.xml and is 101,824 bytes in size.

FIELD OF THE INVENTION

The present invention relates to interference peptides as inhibitors of the interactions connected to the AMPA receptor endocytosis and to peptide compounds of some of those peptides that can be used in medicine, in the field of neurology and psychiatry, in particular for the prevention and therapy of mild cognitive impairment in neurodegenerative diseases and/or in the prophylaxis of depression and anxiety.

BACKGROUND ART

The receptor of the α-amino-3-hydroxy-5-methyl-4-isoxazolepropionic acid, abbreviated as AMPAR or, alternatively, the AMPA receptor, is a glutamate receptor and an ionotropic channel that mediates rapid excitatory synaptic transmission in the central nervous system.

An important number of specialized articles, including Whitlock et al. [1] indicates a role of this receptor in memory and learning through a process called long-term potentiation (LTP).

By long-term potentiation (LTP), the transmission of the nerve signal through the synapse is better due to an above average number of AMPA receptors involved in the process.

As it is known from Guntupalli et al., [2] and Temkin et al. [3], several diseases such as Alzheimer's disease or Parkinson's disease seem to involve a reduced ability to maintain LTP in the synapses. This depreciation is caused by the withdrawal of AMPA receptors from the postsynaptic region involved in signal transmission and their inclusion in formations inside the neuron removed from the synapse, denominated endosomes, through a process called internalization.

Research in the field, such as that of Jang et al. [4], focused on an enzymatic reaction involved in the process of receptor internalization: dephosphorylation of tyrosine 876 from the cytoplasmic tail of the GluA2 subunit of the AMPA receptor by a phosphatase called STEP (striatal-enriched protein tyrosine phosphatase). This post-translational change plays an important role in the cascade of reactions leading to AMPA receptor endocytosis.

Studies by Scholz, R. et al. [5] indicated that, at a later stage of receptor dephosphorylation, in the internalization process, the interaction between GluA2 and BRAG2 (Brefeldin A-resistant Arf Guanine Nucleotide Exchange Factor 2) also plays an important role. Given the role of AMPA receptors in memory (through LTP), efforts have been made in the field to find molecules with therapeutic potential to prevent internalization of the receptor.

Two technical approaches are currently known for inhibiting the dephosphorylation of tyrosine 876 from GluA2.

The first approach involves infusing neurons with specific fragments of GluA2 or derived from GluA2 that interact instead of GluA2 with proteins from the cascade of reactions that lead to internalization, thus reducing the number of proteins in the internalization cascade that end up interacting with the receptor, internalizing it, as disclosed in the patent EP1687427B1 belonging to the holder The University of British Columbia, granted on 24 Aug. 2016.

The second approach, described by Hou et al. [6], but also by Witten et al. [7] and found in the description of the publication of the international patent application WO 2012/037397A2 of 22 Mar. 2012, involves the characterization of the three-dimensional structure of STEP and computer-aided design of molecules that inhibit protease by binding to specific areas of its molecule.

From the international application WO 2012/037397 published on 22 Mar. 2012, it is also known that therapeutic molecules have been created based on a peptide sequence, which is a derivative of STEP and which has the ability to improve and treat cerebral lesions as a consequence of excessive glutamate release and/or oxidative stress, but which are also effective in the treatment and improvement of diseases associated with memory loss. The authors claim an isolated peptide, comprising certain domains of the STEP protein, wherein at least one phosphorylation site in these domains is modified so as to prevent phosphorylation at that site.

Disadvantages of the Prior Art

The molecules developed so far to prevent the internalization of AMPA receptors are either synthetic chemicals with potential adverse effects due to toxicity, or interference peptides whose efficacy has not yet been quantified in terms of the strength of the interaction with STEP phosphatase and BRAG2 protein, or involves blocking a region of the cytoplasmic tail of AMPAR with a STEP derivative, which could adversely interfere with other essential processes occurring in the same area of the receptor. In addition, no research has been reported to date to find therapeutic molecules to target the BRAG2-AMPA receptor interaction.

In the absence of transport sequences embedded in the peptide molecule, the existing interference peptides are relatively long, raising difficult problems with the route and mode of administration as a drug.

The Problem Solved by the Invention

The present invention eliminates the disadvantages set forth in the prior art, by providing shorter interference peptides that would prevent interactions of the AMPA receptors with STEP, but also of BRAG2 with AMPA receptors in neurons, especially synaptic neurons, STEP phosphatase and BRAG2 protein intervening in the sequence of reactions that lead to the internalization of the AMPA receptor.

In addition, the present invention provides short phosphorylated peptides, which can be coupled with a viral sequence as a transport sequence, in order to facilitate the penetration of the cell membrane of neurons, especially synaptic neurons.

An advantage of the invention also consists in the method of inhibiting the endocytosis of the AMPA receptors by using the phosphorylated interference peptides according to the invention.

Therefore, the technical problem solved by the present invention is to develop shorter peptides with high inhibitory activity in the cascade of biochemical processes leading to the endocytosis of the AMPA receptors, having an increased penetrability at cell membrane level which determines their use as active substances in peptide compounds with drug role in the therapy of diseases in which the internalization of AMPA receptors plays an important role.

Terms Used in the Invention

Ach—Acetylcholine
AchE—Acetylcholinesterase
AMPAR—α-amino-3-hydroxy-5-methyl-4-isoxazolpropionic acid receptor
BRAG2—Brefeldin A-resistant Arf Guanine Nucleotide Exchange Factor 2
CNS—central nervous system
DHPG—3,5-dihydroxy-phenyl-glycine
DMSO—dimethyl sulfoxide
DTT—dithiothreitol
F2Pmp—4-(phosphonodifluoromethyl) phenylalanine
FP—fluorescence polarization
GST—Glutathione S Transferase
HEPES—2-[4-(2-hydroxyethyl) piperazin-1-yl] ethane sulfonic acid
IC50—half of the maximum inhibitory concentration
Kd—dissociation constant
Ka—association constant
Ki—inhibition constant
LE—ligand efficiency
LTD—long-term depression
LTP—long-term potentiation
mAChR—muscarinic acetyl choline receptor
mGluR—metabotropic glutamate receptor
NMDAR—N-methyl D-aspartate receptor
PEG—polyethylene glycol
PSD—postsynaptic density
Rmax—maximum response of the device (Biacore™)
RU—response units
Sco—scopolamine
SDS-PAGE—Sodium dodecyl sulfate polyacrylamide gel electrophoresis
SPR—Surface plasmon resonance
STEP—striatal-enriched protein tyrosine phosphatase
STEP32-GluA2-CT complex between STEP32 and the cytoplasmic tail of GluA2
TAT—Trans-activator of transcription of the human immunodeficiency virus
TAM=TAMRA—tetramethylrhodamine
A—alanine
C—cysteine
D—aspartic acid
E—glutamic acid
F—phenylalanine
G—glycine
K—lysine
N—asparagine
Q—glutamine
R—arginine
S—serine
T—threonine
V—valine
W—tryptophan
Y—tyrosine
pY—phosphotyrosine Short Description of the Invention An object of this invention is to develop short peptides with increased chances of crossing the blood-brain barrier, capable of binding to STEP phosphatase, forming a dephosphorylated compound by STEP action to inhibit the formation of the BRAG2-AMPA receptor complex, thus preventing AMPA receptor endocytosis.

To this end, a first object of the present invention relates to an interference peptide with the formula (SEQ ID NO 9)
E-G-Y-N-V-Xa1-Xa2-Xa3 having an inhibitory action on the bond between GluA2 and STEP32 and/or between GluA2 and BRAG2 in neurons, especially synaptic neurons, wherein:

Xa1 represents the Y amino acid which is phosphorylated or non-phosphorylated.

Xa2 represents an amino acid that is missing or that is independently selected from E and G.

Xa3 is an amino acid that is missing when Xa2 is E or that is D when Xa2 is G.

The invention provides a hexapeptide, a heptapeptide and an octapeptide, as such or phosphorylated to a second tyrosine residue as a result of post-translational modifications.

A second object of the invention is a peptide compound comprising a phosphorylated interference peptide, coupled with an amino acid sequence called a transport sequence, for penetrating the cell membrane of neurons, especially synaptic neurons, in order to use the interference peptide according to the invention as a drug.

The invention also provides a third object of the invention, which relates to peptidomimetic compounds of phosphorylated interference peptides to the second tyrosine residue, wherein this residue is replaced by the group 4-(phosphonodifluoromethyl)-L-phenylalanine (F2Pmp), the peptidomimetic compounds mentioned having an inhibitory action on the bonds between GluA2 and STEP in neurons, especially synaptic neurons.

A fourth object of the invention is also provided, which consists of a method of inhibiting of AMPA receptor endocytosis in neurons, especially synaptic neurons using the phosphorylated interference peptides according to the invention, which comprises as successive steps: inhibiting the formation of the AMPA receptor-STEP complex by binding STEP to a phosphorylated interference peptide, dephosphorylation of the compound formed in the previous step under the action of STEP and inhibition by the dephosphorylated compound of the BRAG2-AMPA receptor complex, thus preventing receptor endocytosis.

A fifth object of the invention is also provided, which consists of a Method of inhibiting of AMPA receptor endocytosis in vitro in neurons, especially synaptic neurons, using a peptidomimetic compound according to the invention, by inhibiting the formation of the AMPA receptor-STEP32 complex by binding STEP32 to a peptidomimetic compound and forming a STEP-peptidomimetic compound.

The Advantages of the Invention

The present invention has the following advantages:

The peptides according to the invention are shorter than those existing in the state of the art, having a higher bioavailability and predictably lower toxicity than the STEP protease inhibitors from the state of the art.

The peptides according to the invention are based on polypeptide sequences, which gives them a high chance of having good tolerability and low toxicity as drug substances.

The peptides according to the invention have a double action in neurons, especially synaptic neurons, in the sense of preventing both the interaction of the AMPA receptor with STEP phosphatase, and the interaction between the BRAG2 protein and the receptor, thus preventing the series of cascading biochemical processes that internalize AMPA receptors.

As shown by animal behaviour experiments, by using the peptides according to the invention in pharmaceutical preparations, due to the delay or hindering of the sequence of biochemical processes leading to the internalization of AMPA receptors, the patient's short-term and long-term memory is improved, obtaining, in addition, antidepressant and anxiolytic effects of these peptides coupled with appropriate transport sequences.

The existence of multiple variants of the peptides according to the invention and the corresponding peptide compounds has the advantage of allowing the selection for use as a drug of the appropriate peptides depending on factors such as bioavailability, specificity (minimizing side effects), half-life and potency of the drug.

Finally, the peptides according to the invention have a higher STEP binding strength than the peptides in the state of the art, as demonstrated by the results in Tables 2 and 3.

DESCRIPTION OF THE DRAWINGS

FIG. 3A discloses SEQ ID NO: 79.

p<0.0001; Sco vs. (TAT-)3Y: ##p<0.001, Sco vs. (TAT-)p3Y-sh3: ##p<0.001 and Sco vs. (TAT-)p-fin4: ##p<0.001. 5 adult male rats were used for each treatment group.

Figure 13:
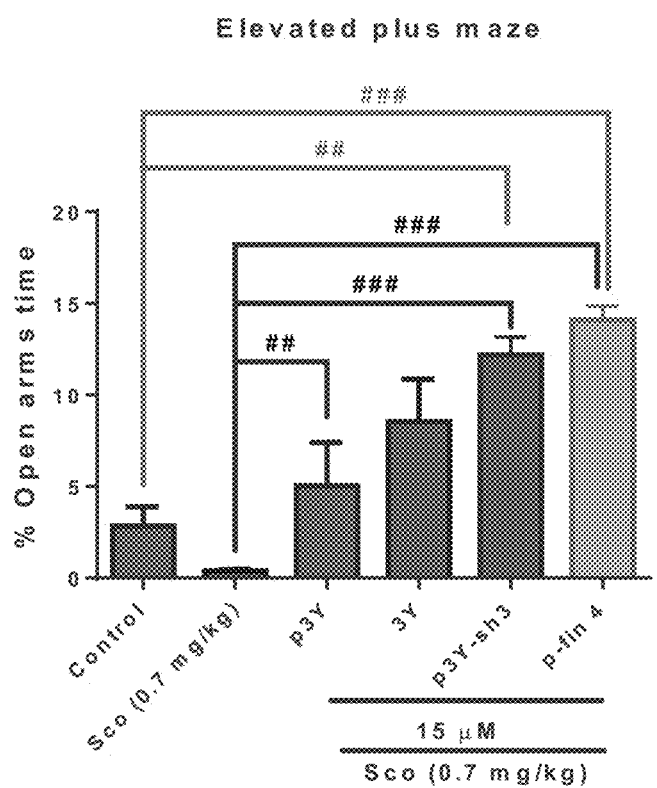

FIG. 13—represents the anxiolytic profile of peptide administration (15 µM) for the time spent in the open arms in the high cross-shaped maze test in mice treated with scopolamine (0.7 mg/kg). Anxiolytic profile of peptide administration (15 µM) on the open arms time % within the elevated plus-maze test in the Sco (0.7 mg/kg)-treated rats. Values are mean±S.E.M (n=5). For Tukey's post hoc multiple comparison test: Sco vs. 3Y: ##p<0.001; Sco vs. p3Y-sh3: ###p<0.0001, and Sco vs. p-fin 4: ###p<0.0001.

Figure 14:
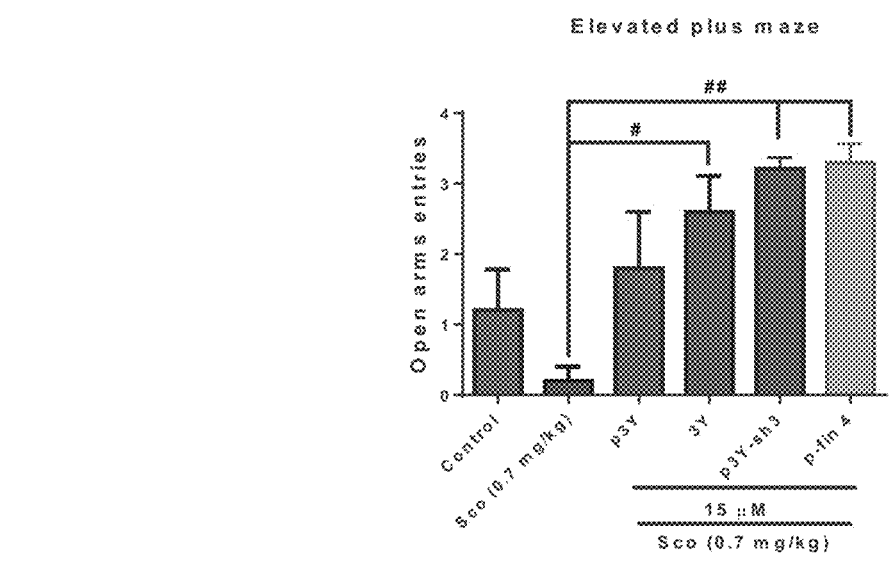

FIG. 14—represents the anxiolytic profile of peptide administration (15 µM) for the number of entries in the open arms in the cross-shaped maze test in mice treated with scopolamine (0.7 mg/kg). Anxiolytic profile of peptide administration (15 µM) on the number of open arms entries within the elevated plus maze test in the Sco (0.7 mg/kg)-treated rats. Values are mean±S.E.M (n=5). For Tukey's post hoc multiple comparison test: Sco vs. (TAT-)3Y: #p<0.01; Sco vs. (TAT-)p3Y-sh3: ##p<0.001, and Sco vs. (TAT-)p-fin4: ##p<0.001. 5 adult male rats were used for each treatment group.

Figure 15:
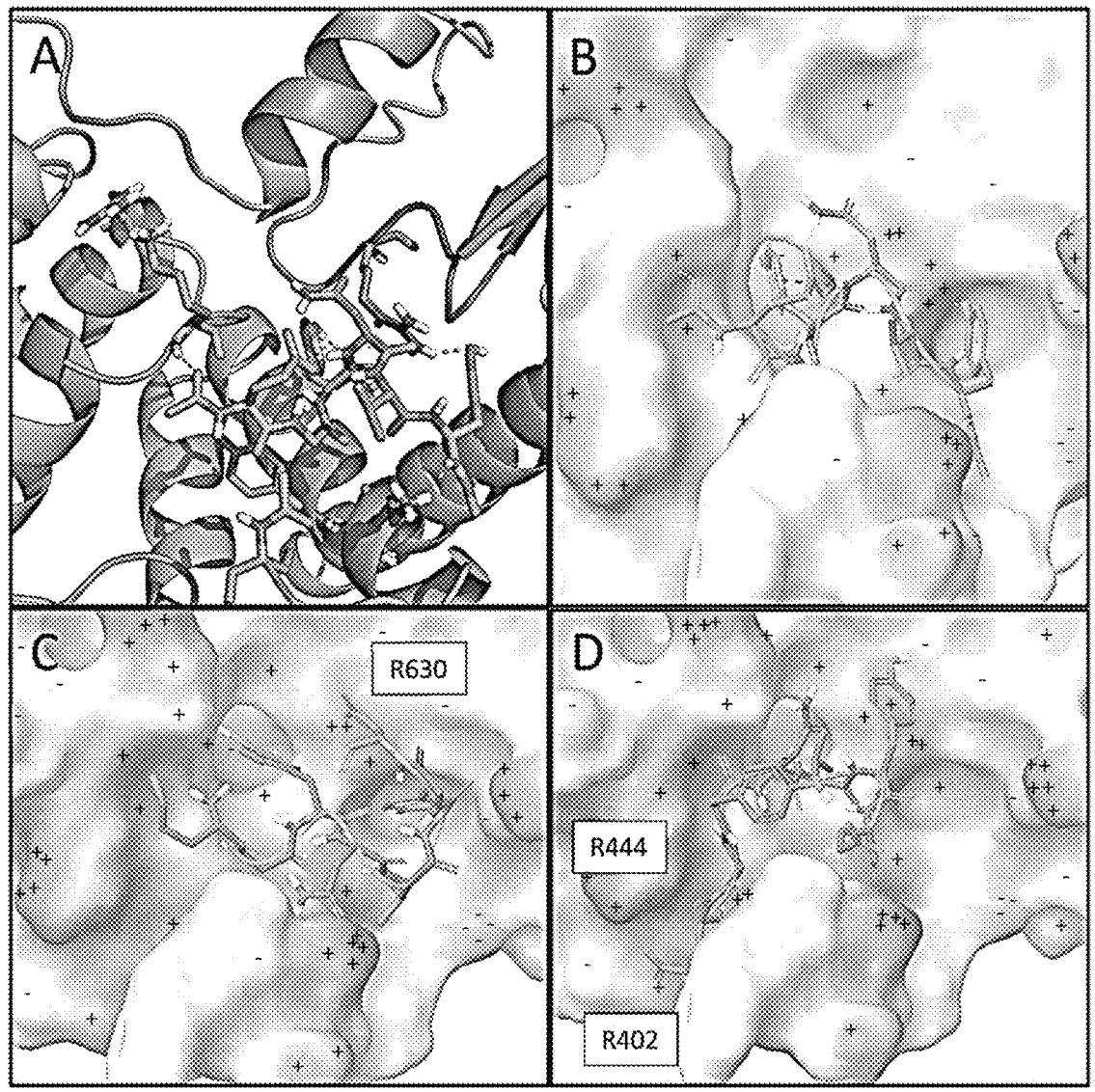

FIG. 15—represents the docked binding positions of hexapeptide, heptapeptide and non-phosphorylated octapeptide at the proposed BRAG2 binding situs. (A) Docked binding pose of the EGYNVY (SEQ ID NO: 4) peptide in the proposed binding site of BRAG2. The peptide establishes multiple H-bonds with BRAG2, as well as a cation-π interaction with the sidechain of the R630 residue (B) In the surface view of BRAG2, it is seen that the two tyrosine residues of the peptide complement two small cavities which are quite difficult to access. (C) EGYNVYGD (SEQ ID NO: 6) peptide has a similar binding mode with EGYNVY (SEQ ID NO: 4) with a supplementary H-bond between the aspartic residue and the R630 of BRAG2 (docking score: −7.327). The EGYNVYE (SEQ ID NO: 5) peptide has a different binding mode, with the N-terminal tail inserted in the tyrosine-binding subpocket identified earlier (docking score: −6.778). This allows the existence of two supplementary H-bonds between the N-terminal glutamate and R402 and R444 of BRAG2 (surfaces marked with "+"). The image was produced with Pymol™ (A) and Maestro™ (B, C, D)[59].

Figure 16:
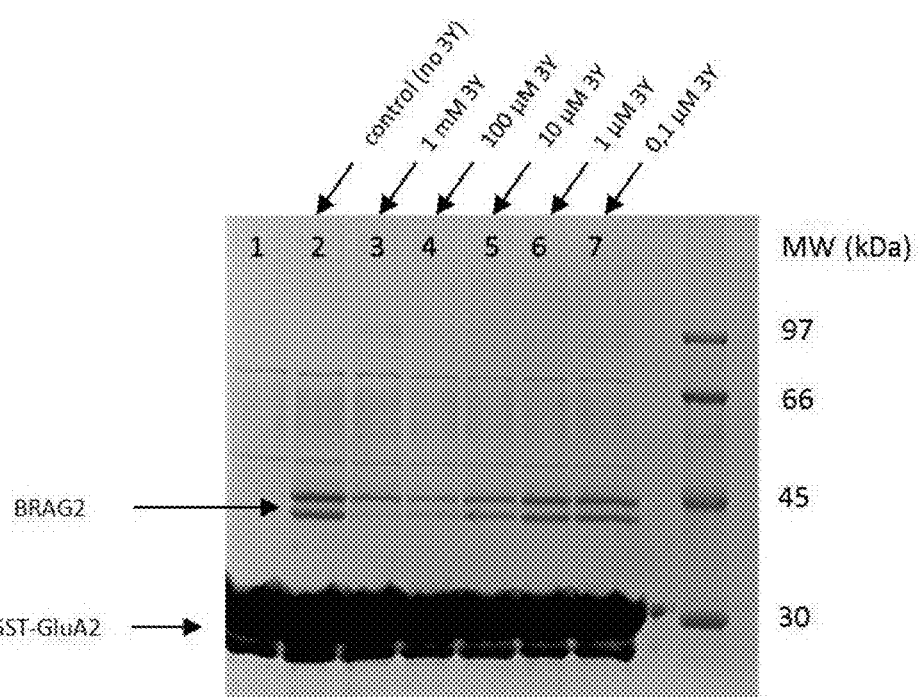

FIG. 16—represents the role of 3Y in disrupting the BRAG2-GluA2 complex. Role of 3Y in disrupting the BRAG2-GluA2 complex. All samples contain GST-GluA2. Lane 1. Control without BRAG2 and without 3Y; Lane 2. Control with BRAG2 and without 3Y; Lanes 3-7. BRAG2 and increasing concentrations of 3Y.

Figure 17:
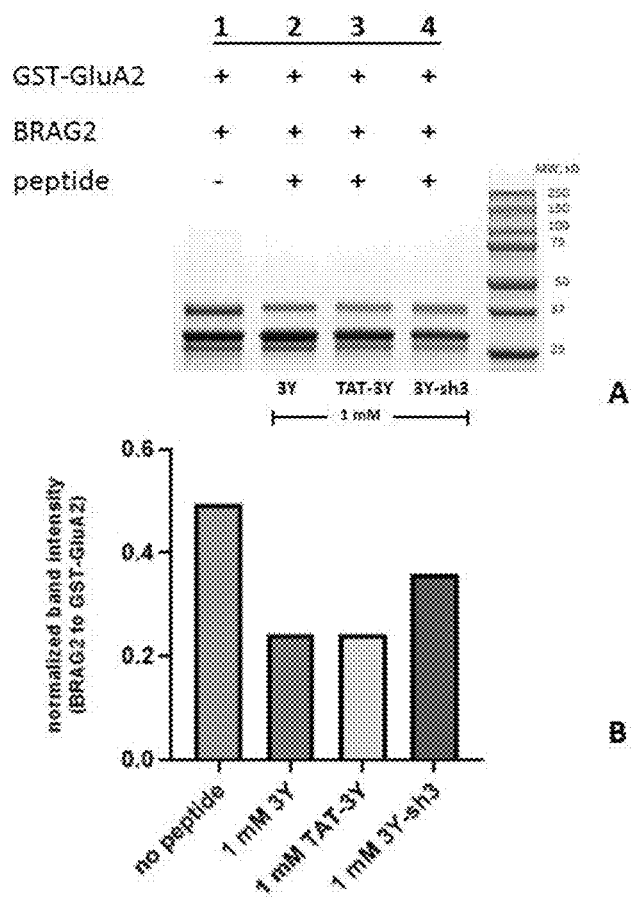

FIG. 17—shows the effect of various peptides on the GST-GluA2-BRAG2 complex. A. SDS-PAGE gel of the species pulled down with GSH Sepharose-coupled GST-GluA2. On the first lane, only BRAG2 was present in the solution containing the beads. On lanes 2-4 the BRAG2 solution also contained 1 mM of different peptides. B. BRAG2 band intensities from A. normalized to the GST-GluA2 band intensities.

DETAILED DESCRIPTION OF THE INVENTION

The decline of cognitive capacity is one of the most debilitating features of degenerative diseases. Growing evidence indicates that changes in synaptic plasticity [8] are key features in these diseases. Synaptic function depends on synaptic plasticity which is believed to underlie memory and learning [9]. Long term changes in synaptic functions can be induced by activation of N-methyl-D-aspartate receptors, short denomination NMDAR or, alternatively denominated NDMA receptors, which modify synaptic strength through regulating the number of postsynaptic α-amino-3-hydroxy-5-methyl-4-isoxazolepropionic acid receptors, short denomination AMPAR, or, alternatively denominated AMPA receptors. NMDAR activation leads to Ca2+ influx through the receptor ion channel which can initiate either long term potentiation (short denomination LTP) or long term depression, short denomination LTD, depending on the spatiotemporal activation profile. As suggested by an increasing number of behavioral studies, cognitive and learning abilities can be evaluated in animal models by modulating LTP in specific regions of the brain [10].

Since synaptic plasticity is governed by AMPAR and NMDAR activity, efforts to control the expression of LTP and LTD are directed to the inhibition or activation of these two receptors. As long as NMDAR can either promote or inhibit LTP, depending on the activation pattern of the receptor, controlling its activity is insufficient for experimental setups in which regulating the expression of LTP and LTD is needed. On the other hand, controlling AMPAR activity is a more straightforward approach in engineering synaptic plasticity, since an increased number of AMPARs, but not NMDARs, is characteristic to LTP expression [11].

AMPARs are glutamate-activated ion channels which mediate the fast synaptic transmission in the central nervous system (CNS). An increased number of postsynaptic AMPARs is delivered to the synaptic density during LTP [11], while LTD causes a decrease in the number of AMPARs clustered at the synapses [12]. AMPAR trafficking is a complex process, regulated by numerous protein interactions and various signaling pathways. Upon LTP stimulation, exocytosis of AMPAR and diffusion of these receptors from exocytic sites toward postsynaptic density (PSD) enrich the pool of AMPA receptors able to participate in synapses [13]. Conversely, during LTD, AMPAR diffuses away from the PSD and receptor endocytosis takes place [14].

AMPAR consists of four types of subunits, designated GluA1-GluA4. They generally assemble into heterotetrameric structures formed by joining two homodimers. In the hippocampal CA1, which is probably the most studied synaptic region, cca. 80% of the AMPARs consist of GluA1-GluA1-GluA2-GluA2 tetrameric assemblies. Furthermore, it is this assembly that primarily mediates the synaptic transmission [15]. The four subunits have a high homology, with 70% sequence identity [16]. However, there are major differences in the cytosolic tails of the subunits, and these differences govern the protein-protein interactions that are involved in receptor trafficking. Indeed, the majority of the important interactors involved in synaptic plasticity bind the C-terminal tail of GluA2, which makes this subunit a key player in the expression of LTD [17], [18].

To solve the technical problem, a first object of the present invention relates to an interference peptide of the formula (SEQ ID NO: 9)
E-G-Y-N-V-Xa1-Xa2-Xa3, having inhibitory action on the bonds between GluA2 and STEP32, where STEP32 is the truncated version, of 32 kDa of STEP phosphatase and/or between GluA2 and BRAG2 in neurons
in which:
Xa1 represents amino acid Y which is phosphorylated or non-phosphorylated.
Xa2 represents an amino acid that is missing or that is independently selected between E and G;
Xa3 is an amino acid that is missing when Xa2 is E or that is D when Xa2 is G.

The peptides of the invention are short peptides such as a hexapeptide, a heptapeptide or an octapeptide, with increased chances of crossing the blood-brain barrier. In certain embodiments, each of the peptides of the invention undergoes a post-translational modification, being phosphorylated to the second tyrosine residue, as follows:

In one embodiment of the invention, the interference peptide is the hexapeptide

E-G-Y-N-V-Y (SEQ ID NO: 4)

In another embodiment of the invention, the interference peptide is the hexapeptide E-G-Y-N-V-pY (SEQ ID NO: 1)

wherein pY represents phosphorylated Y

In another embodiment of the invention, the interference peptide is the heptapeptide with the formula

E-G-Y-N-V-Y-E (SEQ ID NO: 5)

In another embodiment of the invention, the interference peptide is the heptapeptide with the formula E-G-Y-N-V-pY-E (SEQ ID NO: 2)

wherein pY represents phosphorylated Y

In another embodiment of the invention, the interference peptide is the octapeptide with the formula

E-G-Y-N-V-Y-G-D (SEQ ID NO: 6)

In another embodiment of the invention, the interference peptide is the octapeptide with the formula E-G-Y-N-V-pY-G-D (SEQ ID NO: 3)

wherein pY represents phosphorylated Y.

Specific post-translational modifications such as threonine, serine and tyrosine phosphorylation play a regulatory role in this process, by favoring or hindering interactions between the C-tail of the receptor and other proteins, as reviewed by Diering & Huganir [17].

In electrophysiological setups, synaptic plasticity can be studied by inducing two principal types of LTD: mGluR-dependent LTD and NMDAR-dependent LTD [10]. Both types of LTD depend upon distinct post-translational modifications on GluA1 or GluA2. Several studies indicate that NMDAR-dependent LTD can occur because Y876 of GluA2 is phosphorylated [19], [20]. On the other hand, mGluR-dependent LTD (or more specifically DHPG-LTD) depends on the dephosphorylation of the same Y876 located in the cytoplasmic, C-terminal region of GluA2 (GluA2-CT) [21]. Interestingly, Scholz et al.[5] demonstrated that both mGluR- and NMDAR-LTD rely on GluA2-BRAG interaction. Dephosphorylation of Y876 was found essential for this interaction and implicitly for AMPAR clathrin-mediated endocytosis [5]. This important result explains why GluA2 3Y (YKEGYNVYG (SEQ ID NO: 11)), a short segment of GluA2-CT, and other interference peptides can disrupt the interactions between GluA2 and the endocytic mechanisms [10], [22], [19], [23], [24], [25], [26]. In line with these findings, dephosphorylation of GluA2 Y876 by megakaryocyte protein tyrosine phosphatase (PTPMEG) and by striatal-enriched tyrosine phosphatase (STEP, PTPN5) were found necessary for cerebellar LTD and the hippocampal LTD [28], respectively. Furthermore, phosphorylation of Y876 seems to play a role in AMPARs synaptic anchoring in the PSD. The receptor localization at the postsynaptic density depends on the glutamate receptor interacting protein (GRIP). Specifically, GRIP1 interacts with GluA2 stabilizing it in the PSD, only as long as S880 on GluA2 is not phosphorylated [29]. On the other hand, phosphorylation of S880 needs Y876 to be dephosphorylated, at least in Purkinje cells and cerebellar LTD [21]. Thus, the localization of the AMPAR at the synapse is higher when Y876 is phosphorylated. Dephosphorylation of Y876 seems to play a critical role in inducing AMPAR internalization and, hence, in LTD expression. Consequently, inhibiting phosphorylation of Y876 would preclude AMPAR endocytosis, hence LTD, and could improve cognitive abilities. Indeed, it has been reported that genetic reduction of STEP phosphatase in triple transgenic AD mouse model improved cognitive performance paving the way towards rational drug design [7].

In an attempt to find novel, highly efficient inhibitors of AMPAR internalization, the mode of action by which the peptides according to the invention are able to prevent the interaction of STEP—GluA2-CT, and, consequently, to prevent the internalization of AMPA receptors, is further detailed.

Hexapeptide, heptapeptide and octapeptide according to variants of the invention have been identified as effective in vitro inhibitors of STEP interaction with GluA2-CT. In vivo experiments were performed with phosphorylated hexapeptide and heptapeptide and evidenced that both peptides restore the memory deficits and display anxiolytic and antidepressant effects in a scopolamine treated rat model. These experimental results that we will present here demonstrate that the interference peptides which disrupt STEP-GluA2 protein-protein interaction are viable starting points for developing new and therapeutically efficient cognitive enhancers and/or behavioral modulators.

Computational Modeling of the Interaction Between the STEP Active Site and the Cytoplasmic Segment of the AMPA GluA2 Subunit The purpose of the invention is to supply peptides that prevent the interactions of the AMPA receptors with STEP or of BRAG2 with AMPA receptors. These interactions are a part of the sequence of processes that lead to the internalization of the AMPA receptor. A possible solution is presented below:

In the first stage, the protein-protein interactions between the STEP phosphatase and the GluA2 subunit of the AMPA receptor are prevented, with the help of a phosphorylated interference peptide, i.e. a competitor, the term "competitor"

expressing the quality of a species to disrupt this complex. At this stage, the peptide binds to STEP instead of AMPAR. Following interaction with STEP, the interference peptide undergoes dephosphorylation. Following dephosphorylation, the peptide acquires a form capable of interacting with BRAG2. In the last step, by binding the peptide to BRAG2, the interaction of the latter with AMPAR is prevented.

For this purpose, the inventors first developed a computational model of the interacting protein surfaces of the embodiment in which pY is phosphorylated tyrosine and in which the interference peptides act on the bonds between GluA2 and STEP32. STEP dephosphorylates Glu2A at Y876 located in the cytoplasmic tail that has the following sequence:

(SEQ ID NO: 12)
IEFCYKSRAEAKRMKVAKNAQNINPSSSQ
NSQNF<u>ATYKEGYNVYGI</u>ESVKI

Here, bold letters denote the longest sequence of the cytoplasmic domain that is present in an experimental structure of AMPAR (PDB Code: 5KK2) [31], and the Yin the 44th position from the NVYG sequence (SEQ ID NO: 13) is the phosphorylation site (Y876). The underlined fragment is a peptide with the length of 11 amino acids termed "3Y peptide" or simply "3Y" due to its three tyrosine residues, that was shown to bind to BRAG2 [5] and was used as a model system for this invention.

Since a protein BLAST [32][33] search has revealed the complete unavailability of a structural template for the whole cytoplasmic segment (apart from the first part indicated in bold), the inventors have applied the underlined fragment for the studies presented here.

It has been shown that STEP dephosphorylates glutamate receptor subunits GluN2B and GluA2 [34]. Dephosphorylation leads to the internalization of ionotropic glutamate receptors, which in their turn withholds synaptic strengthening.

The 3D structure of STEP has been resolved with X-ray crystallography: currently, there are three publicly available structures: 2BIJ, 2BV5 and 2CJZ [36]. From the point of view of protein tyrosine phosphatase catalytic activity, one of the most important fragments of the STEP protein is the so-called "signature motif", (I/V)HCXAGXGR(S/T) (SEQ ID NO: 14), which contains a catalytically essential arginine residue (R478), and forms a rigid cradle-like structure that coordinates the phosphate group of the substrate [35]. The phosphate-binding cradle (formed by the surrounding R478 residues) allows the establishment of multiple salt bridges and hydrogen bonds with a negatively charged moiety, such as the phosphate group from the substrate, or a suitable isostere. In the PDB structure of 2CJZ, the catalytically inactive C472S mutant of STEP is co-crystallized with a phosphotyrosine in the catalytic site; due to the better orientation of the catalytic arginine in comparison with the other structures (see FIG. 1B), the inventors have selected this structure for modeling purposes [35].

The inventors have defined the STEP binding site based on the location of the phosphotyrosine ligand in the PDB structure 2CJZ. To establish a computational modeling framework for the binding of peptides to the binding site of STEP, conformational ensembles for the unphosphorylated and the Y876-phosphorylated 3Y peptide (p3Y) were generated, and used the rigid docking mode of Glide to propose possible binding modes.

Figure 2A:
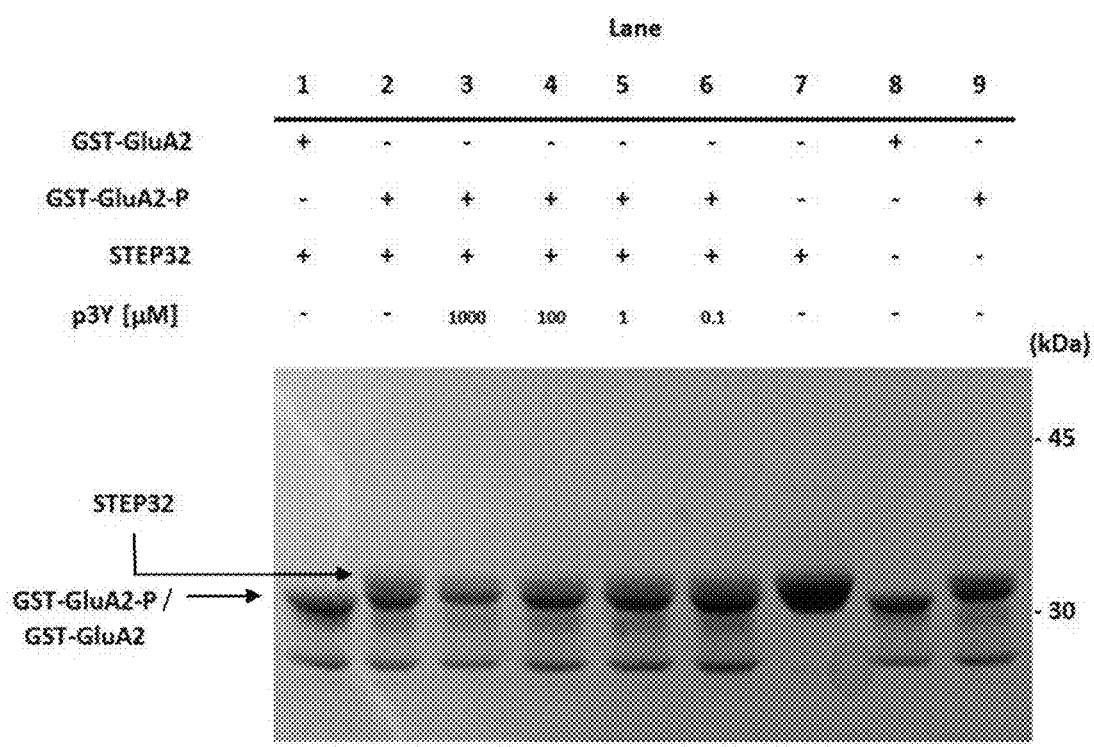
FIG. 2A—represents the pulldown test of phosphorylated GST-GluA2 and STEP32 outlining the competing effect of phosphorylated 3Y peptide (p3Y). Pulldown assay for phosphorylated GST-GluA2 and STEP32 outlining the competing effect of the phosphorylated 3Y peptide (p3Y). Lane (1) shows that unphosphorylated GST-GluA2 bound to Glutathione Sepharose beads cannot pull down STEP32. Lane (2) shows that STEP32 is bound to phosphorylated GST-GluA2. Resemblance of MW of STEP32 (lane 7) and phosphorylated GST-GluA2 with traces of unphosphorylated GST-GluA2 (lane 9) is evident, but the presence of STEP32 is distinguishable. Decreasing the 3Y-P concentration from 1000 µM to 0.1 µM (lanes 3-6) leads to increased intensity of the upper band, that is a higher amount of pulled down STEP32.
Figure 2B:
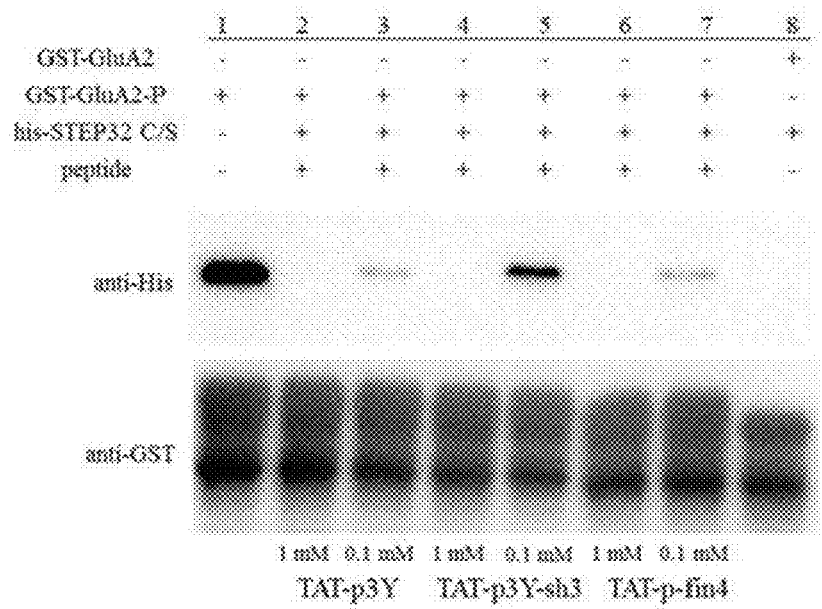
FIG. 2B—shows typical results from a pull-down experiment using GSH-Sepharose bound phosphorylated GST-GluA2 to pull down the His-tagged inactive mutant of STEP32 (C/S). Two concentrations from the peptides TAT-p3Y, TAT-p3Y-sh3 and TAT-p-fin4 were used in two different concentrations to hinder the binding of STEP32 C/S to GluA2. On lane 1 the samples contained no peptide. As a negative control, on lane 8 unphosphorylated GST-GluA2 was used to pull-down STEP32. The lower band on anti-GST blotting corresponds to C-terminally truncated form of GluA2-CT which could not be removed during purification.
Figure 2C:
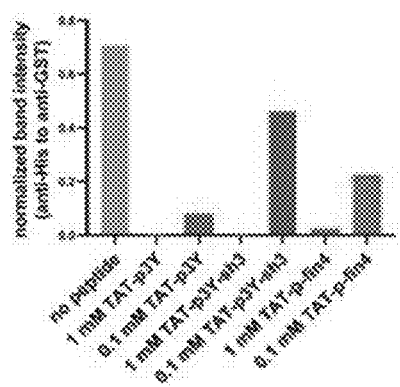
FIG. 2C—shows normalized (to anti-GST signals) mean values for the band intensities of anti-His from A reflecting the amount of STEP32 C/S bound to phosphorylated GST-GluA2 in presence of various concentrations of peptides. Two replicate experiments were performed.
Figure 2D:
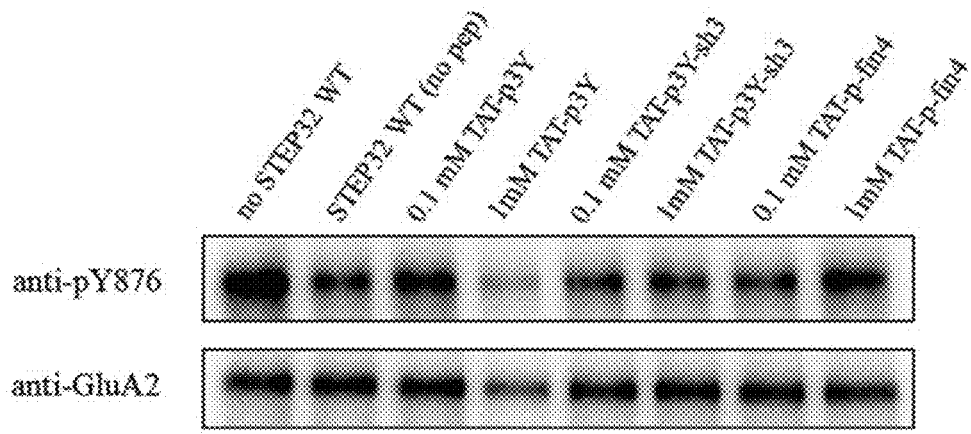
FIG. 2D—shows inhibition of pY876 GluA2 FL dephosphorylation by STEP32 WT in presence of the TAT-phosphopeptides (TAT-p3Y, TAT-p3Y-sh3 and TAT-p-fin4). A. Representative blot of three independent experiments. GluA2-FL phosphorylated at Y876 site was immunoprecipitated from HEK293T cells overexpressing GluA2 and vSrc using anti-GluA2 antibodies and then submitted to in vitro dephosphorylation by purified STEP32 WT, in presence versus absence of TAT-phosphopeptides: TAT-p3Y, TAT-p3Y-sh3 and TAT-p-fin4. The dephosphorylation of the pY876 site of GluA2 FL was detected by western blotting using anti-pY876 antibodies and anti-GluA2 antibodies.
Figure 2E:
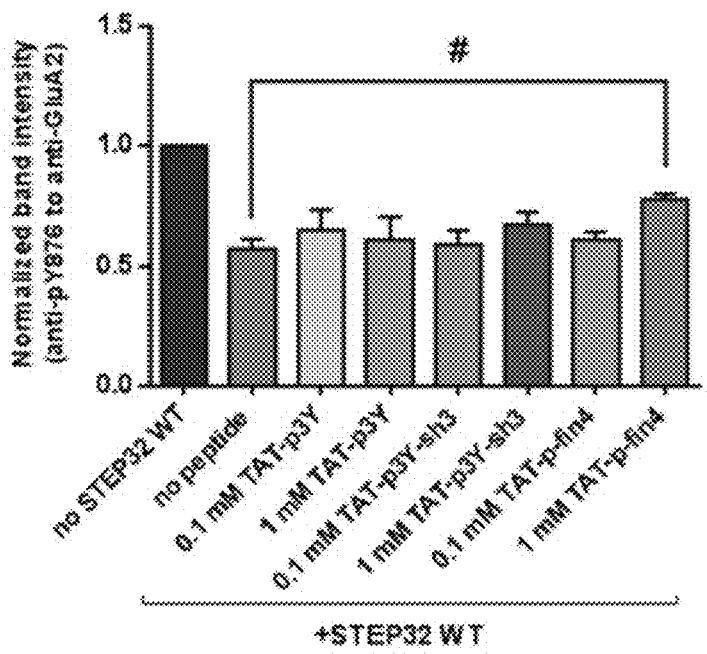
FIG. 2E—shows a bar graph representing the band intensity of pY876 normalized to total GluA2 FL for each sample and to the signal of control, untreated with STEP32 WT (no STEP32 WT). The results represent mean±SEM of three independent experiments. The statistical significance was assessed using unpaired t-test with Welch's correction: no peptide sample vs. 1 mM TAT-p-fin4+STEP32 WT sample: # $P<0.05$.
Figure 2F:
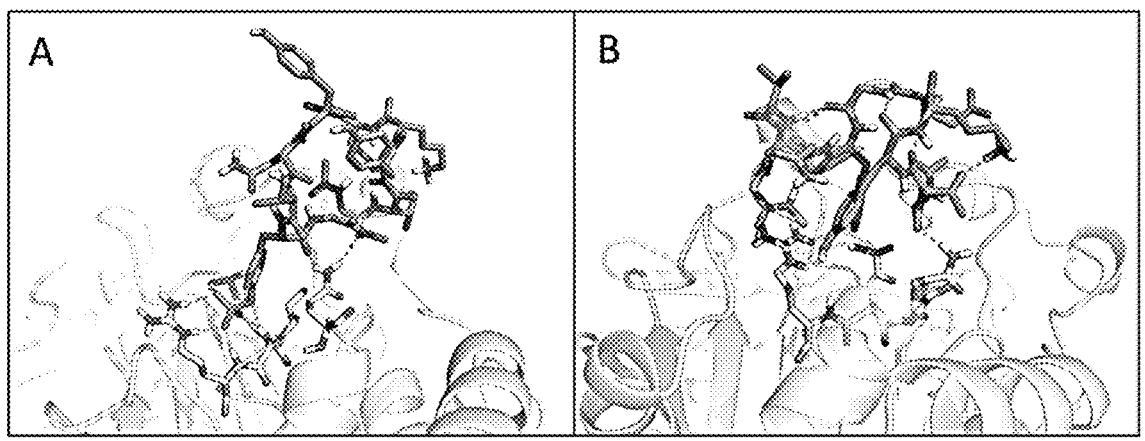
FIG. 2F—represents the predicted binding positions of phosphorylated (A) and non-phosphorylated (B) 3Y peptide to STEP. Predicted binding poses of the phosphorylated (A) and unphosphorylated (B) 3Y peptide to STEP. While multiple charged and H-bond interactions stabilize the phosphorylated segment, the phosphate cavity is not complemented and only two surface H-bonds are established with the unphosphorylated segment.

Docking of the conformational ensembles to the STEP binding site has highlighted the importance of the phosphate group for ligand recognition: the phosphorylated 3Y peptide has produced a binding pose where all of the anchoring interactions are present, whereas the unphosphorylated segment could not fit into this cradle (FIG. 2F). This is easily interpreted by the fact that the main function of STEP (and of phosphatases in general) is the removal of the phosphoryl group, which obviously requires the presence of such a phosphoryl group in the substrate. Docking has also highlighted the residue Q516 as a possible interaction point for both peptides.

Figure 1A:
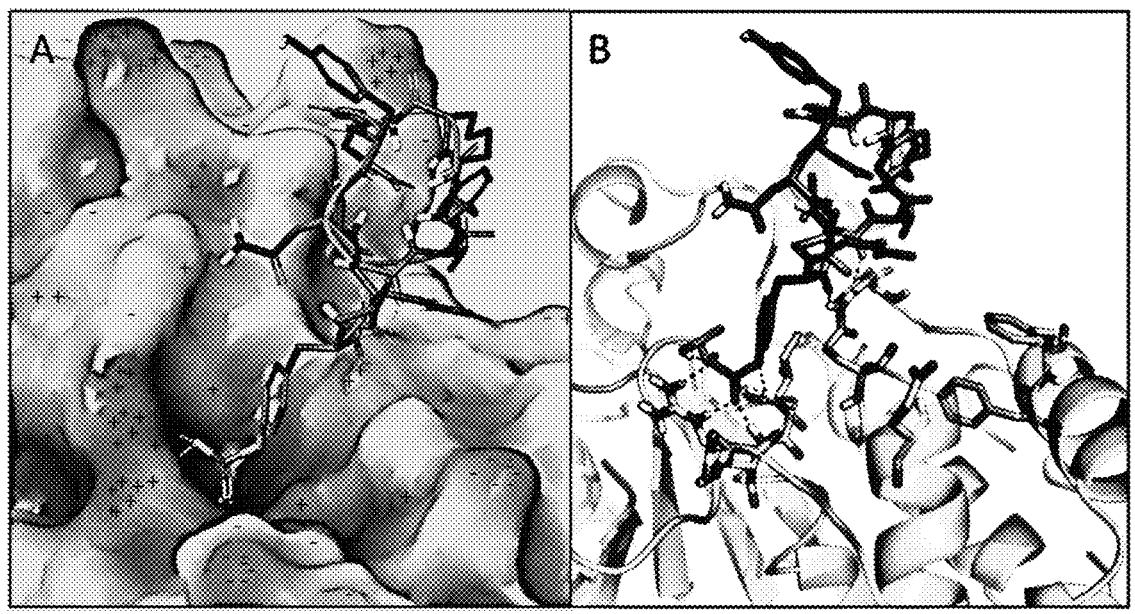
FIG. 1A—represents the binding situs of STEP with phosphorylated 3Y peptide (p3Y). The binding site of STEP in surface (A) and stick and ribbon representations (B), with phosphorylated 3Y peptide (p3Y) shown as grey sticks. The surface is marked with "+" and "−" signs according to the electrostatic potential, i.e. parts marked with "+" correspond to positively charged residues and those marked with "−" correspond to negatively charged residues, such as D437 and E519 (A). The mentioned phenylalanine-rich motif is visible on the right-hand side of the image (B).
Figure 1B:
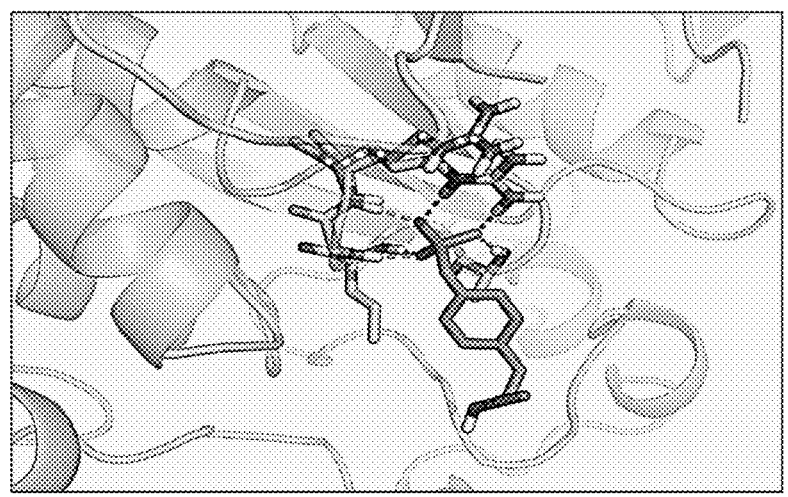
FIG. 1B—comparatively represents the crystalline structures of STEP. Comparison of STEP crystal structures. The catalytic arginine—together with the neighboring residues—stabilizes the bound phosphotyrosine with multiple salt bridges and hydrogen bonds (PDB: 2CJZ). The orientation of the R478 in PDB structure 2BIJ is included for comparison and represented with a white dotted line.

In addition to the phosphate-binding cradle, negatively charged surface residues in the vicinity (D437, E519) could be utilized to establish stabilizing interactions. This use implies the applicability of zwitterionic small molecules or peptides as protein-protein interaction (PPI) inhibitors, with the two oppositely charged groups being relatively close to each other. Additionally, a phenylalanine-rich motif in the vicinity of Q516 could serve as an anchoring site for an aromatic ring via π-π interactions. The binding site features are illustrated in FIG. 1A.

Dissociation of the Complex of STEP and GluA2-CT by the 3Y Peptide

To investigate the interaction between the glutathione-S-transferase (GST) tagged GluA2 and STEP32 there are two alternatives:
first, to use an inactive STEP mutant and GluA2 phosphorylated at Y876 or
second, to use the active form of STEP32 and a non-hydrolysable phosphotyrosine-analogue form of 3Y.

For cost-efficiency reasons the inventors choose the first alternative, which is the tyrosine-phosphorylated GluA2 and the catalytically inactive mutant form STEP32 C/S in which the cysteine from the active site of STEP32 has been changed with serine. This is a trapping mutant, which binds but does not dephosphorylate its substrate, GluA2. Notably, GST-GluA2 has to be phosphorylated (FIG. 3B) in order to interact with STEP32. The competing agent, the 3Y peptide, has to be phosphorylated as well.

To evaluate the dissociating effect of p3Y the inventors have set up in solution the complex between STEP32 and tyrosine-phosphorylated GST-GluA2-CT (GST-GluA2-P) in the presence of various concentrations of p3Y. Then, the non-dissociated complex between GST-GluA2-P and STEP was pulled down using Glutathione-Sepharose. FIG. 2A shows that the higher the p3Y concentration, the weaker the STEP32 corresponding band, reflecting that less STEP32 remained in complex with GST-GluA2-P.

The invention also refers to peptidomimetic compounds of phosphorylated interference peptides at the second tyrosine residue, wherein this residue is replaced by the group 4-(phosphonodifluoromethyl)-L-phenylalanine (F2Pmp), said peptidomimetic compounds having inhibitory action on GluA2 and STEP in neurons.

Figure 3A:
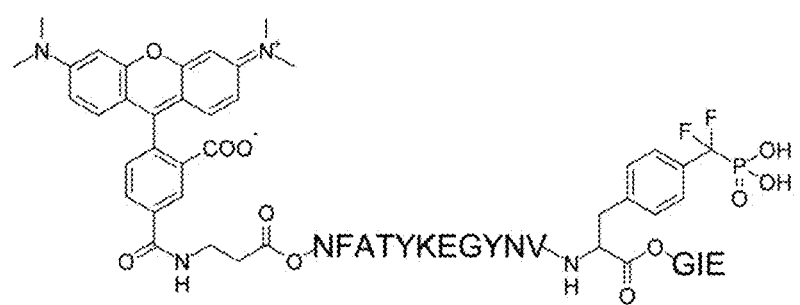
FIG. 3A—represents the structure and sequence of the peptide modified with TAMRA-3Y-F2Pmp used in fluorescence polarization experiments. Structure and sequence of the TAMRA-3Y-F2Pmp modified peptide used in the fluorescence polarization experiments.
Figure 3B:
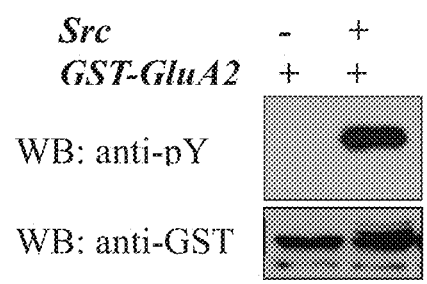
FIG. 3B—represents the tyrosine phosphorylation of the recombinant GST-GluA2 protein using Src kinase in the presence of ATP. Tyrosine phosphorylation of GST-GluA2 using Src kinase. Recombinant GST-GluA2 protein was phosphorylated by Src kinase in presence of ATP. A negative reaction containing GST-GluA2 but not Src kinase was prepared as a negative control. Tyrosine phosphorylation of GST-GluA2 was checked by western blotting using anti-pTyr antibody and the membrane was further reprobed with anti-GST antibodies to confirm the presence of GST-GluA2 protein.

Testing the Capacity of Ala-Scan 3Y Peptides to Dissociate the Complex Between STEP32 and a Fluorescently Labelled 3Y-F2Pmp Peptide To estimate the contribution of each amino acid residue in the 3Y peptide sequence to the overall binding affinity of 3Y, an Ala-Scan experiment has been performed. The third phosphorylated tyrosine in the 3Y sequence was not replaced with Alanine since this tyrosine rest is indispensable for the interaction 3Y with STEP. The sequences of the Ala-scan peptides synthesized are reported in Table 1. Initially, using fluorescence polarization measurements, the inventors evaluated the ability of these peptides to dissociate in a competitive manner the complex between the catalytic domain of STEP (STEP32) and the 3Y peptide N-terminally labelled with the TAMRA fluorophore (TAM-3Y-F2Pmp) (FIG. 3A).

The more successfully a peptide disrupts the complex, the more fluorophore labelled 3Y-P (TAM-3Y-F2Pmp) will be released. The amount of released TAM-3Y-F2Pmp is correlated with an increase in fluorescence polarization, which is experimentally monitored. The inhibitory strength of each peptide is reflected in the value of the inhibition constant $K_i$, which was calculated as described in the Experimental section.

TABLE 1

Results of the inhibitory effect of the Ala-scan peptides on the TAM-3Y-F2Pmp-STEP32 complex

| Name | Sequence | $K_i$ [µM] |
| --- | --- | --- |
| p3Y | ATYKEGYNVpYG (SEQ ID NO: 15) | 2.82 |
| p3YAla2 | AAYKEGYNVpYG (SEQ ID NO: 16) | 1.62 |
| p3YAla3 | ATAKEGYNVpYG (SEQ ID NO: 17) | 4.81 |
| p3YAla4 | ATYAEGYNVpYG (SEQ ID NO: 18) | 2.53 |
| p3YAla5 | ATYKAGYNVpYG (SEQ ID NO: 19) | 4.14 |
| p3YAla6 | ATYKEAYNVpYG (SEQ ID NO: 20) | 2.31 |
| p3YAla7 | ATYKEGANVpYG (SEQ ID NO: 21) | 4.45 |
| p3YAla8 | ATYKEGYAVpYG (SEQ ID NO: 22) | 2.47 |
| p3YAla9 | ATYKEGYNApYG (SEQ ID NO: 23) | 5.94 |
| p3YAla10 | ATYKEGYNVpYA (SEQ ID NO: 24) | 2.71 |

Three peptides, namely p3YAla3, p3YAla7 and p3YAla9 are significantly weaker competitors than p3Y. Two of them have a tyrosine replaced with alanine and the third one has a valine replaced with alanine. The p3YAla5 peptide, with an alanine substituting a glutamic acid residue at position Y5, displays a moderate increase of the inhibition constant.

These results suggest that these particular positions Y3, Y7 and V9 play a more important role than the other amino acids in establishing the interaction with STEP32 C/S. Remarkably, the substitution of the other positions, i.e. T2, K4, G6, N8 and G11 leads to negligible loss of the inhibition capacity of 3Y peptide (and even to a moderate improvement in the case of T2). This result suggests that the latter positions can be substituted in the 3Y sequence with the desired amino acid residues (i.e. for additional intended effects), without deteriorating the interaction with STEP32. These findings were utilized for the design and modeling of virtual peptide libraries based on the 3Y peptide.

Generation of Modified p3Y-Derviatives to Dissociate the STEP-GluA2-CT Complex

The next objective of the inventors was to find shortened or modified derivatives of the p3Y peptide with increased affinity for STEP32. Expectedly, shorter peptides have a higher chance to pass the blood-brain barrier and to elicit the desired functional response. Furthermore, determining the minimal peptide pharmacophore required for binding at the STEP-GluA2 protein-protein interface would facilitate the design of peptidomimetic compounds based on non-peptidic small molecule inhibitors.

For this purpose, a docking study was performed evaluating a series of shortened peptides derived from the original p3Y at the catalytic site of STEP (STEP32). Using the modeling approach detailed earlier, the inventors have docked a total of 49,528 conformations of shortened peptides derived from the original p3Y (see Table S1) to the binding site of STEP.

TABLE S1

Sequences and number of conformations of modified p3Y derivatives. pY denominates a phosphorylated tyrosine, and the mutagenized residues are underlined.

| Sequence | Number of conformations | Sequence | Number of conformations |
| --- | --- | --- | --- |
| Shorter segments of p3Y for the study of the binding with STEP | | | |
| TYKEGYNVpYG (SEQ ID NO: 25) | 1497 | ATYKEGYNVpY (SEQ ID NO: 26) | 1541 |
| YKEGYNVpYG (SEQ ID NO: 27) | 3419 | TYKEGYNVpY (SEQ ID NO: 28) | 1949 |
| KEGYNVpYG (SEQ ID NO: 29) | 1473 | YKEGYNVpY (SEQ ID NO: 30) | 2106 |
| EGYNVpYG (SEQ ID NO: 31) | 2766 | KEGYNVpY (SEQ ID NO: 32) | 1925 |
| GYNVpYG (SEQ ID NO: 33) | 3774 | EGYNVpY (SEQ ID NO: 1) | 3293 |
| YNVpYG (SEQ ID NO: 34) | 2731 | GYNVpY (SEQ ID NO: 10) | 4201 |
| NVpYG (SEQ ID NO: 35) | 5469 | YNVpY (SEQ ID NO: 36) | 4453 |

TABLE S1-continued

Sequences and number of conformations of modified p3Y derivatives. pY denominates a phosphorylated tyrosine, and the mutagenized residues are underlined.

| Sequence | Number of conformations | Sequence | Number of conformations |
|---|---|---|---|
| Optimization of p3Y derivatives for STE 2 binding | | | |
| YNRpY (SEQ ID NO: 37) | 1778 | FGYNDpYG (SEQ ID NO: 38) | 2734 |
| YNKpY (SEQ ID NO: 39) | 2771 | EKYNDpYG (SEQ ID NO: 40) | 850 |
| NTpYG (SEQ ID NO: 41) | 4783 | FKYNDpYG (SEQ ID NO: 42) | 1867 |
| NSpYG (SEQ ID NO: 43) | 2735 | EKYNVpYG (SEQ ID NO: 44) | 1279 |
| GYNVpYR (SEQ ID NO: 45) | 2050 | FGYNVpYG (SEQ ID NO: 46) | 3816 |
| GYNVpYK (SEQ ID NO: 47) | 2967 | FKYNVpYG (SEQ ID NO: 48) | 1945 |
| YVpYG (SEQ ID NO: 49) | 4226 | FTpYG (SEQ ID NO: 50) | 4995 |
| KVpYG (SEQ ID NO: 51) | 2240 | FSpYG (SEQ ID NO: 52) | 5281 |
| FVpYG (SEQ ID NO: 53) | 4993 | WTpYG (SEQ ID NO: 54) | 5218 |
| KGYNVpYG (SEQ ID NO: 55) | 1633 | WSpYG (SEQ ID NO: 56) | 5649 |
| KGYDVpYG (SEQ ID NO: 57) | 1437 | YTpYG (SEQ ID NO: 58) | 4043 |
| GYDVpYG (SEQ ID NO: 59) | 4249 | YSpYG (SEQ ID NO: 60) | 4622 |
| EGYNDpYG (SEQ ID NO: 61) | 2280 | | |

The shorter segments often produced binding poses with a more favorable binding score than the original p3Y peptide, with docking scores as low as −8.7 for some of them. By comparison, the docking score of p3Y was −6.4.

Figure 4A:
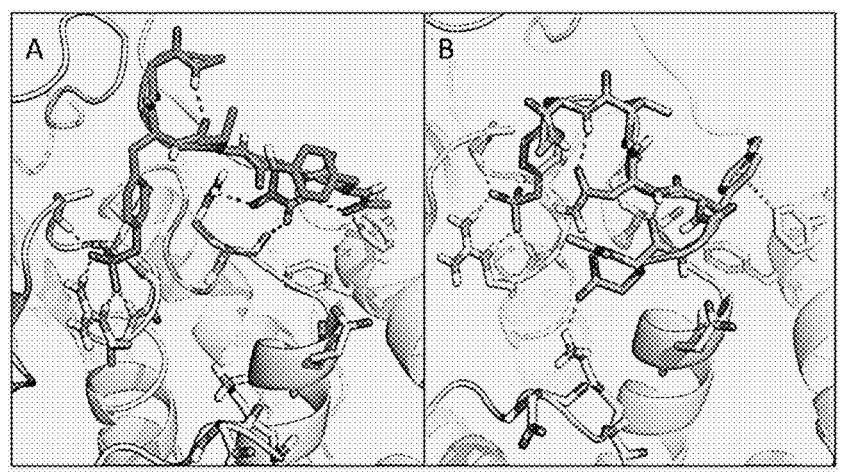
FIG. 4A—represents examples of proposed short peptides that interact with the STEP phosphatase binding situs. Two examples of the proposed short peptides interacting with the binding site of the STEP phosphatase. In addition to binding to the phosphate cradle, the tyrosine residue of the YNVpYG (SEQ ID NO: 34) peptide also forms hydrogen bonds with Q516 of STEP (A), while the peptide EGYNVpY (SEQ ID NO: 1) establishes a H-bond/salt bridge with K439, as well as a stacking interaction between its tyrosine residue and F281 of STEP (B).

Generally, the shorter segments (4-6 amino acids) dominate the best scored poses, a notable exception being the heptapeptide EGYNVpYG (SEQ ID NO: 31) (this finding also correlates with the fact that generally more conformations were generated for the shorter segments, see Table 51). There was no clear preference between the two series of peptides, i.e. with and without the terminal glycine. Afterwards, the inventors have visually assessed the best-scored binding poses and selected the most promising peptides for further consideration, two examples being shown in FIG. 4A.

During the visual evaluation, the following criteria were taken into account:
- the interaction between the phosphate group on the phosphotyrosine and the phosphate cavity of STEP was an absolute necessity.
- any other significant interaction with additional residues from the binding site was considered an advantage. This includes possible interactions with Q516, as well as potential additional interaction points such as the two acidic side chains (D437, E519) and the aromatic residues (F280, F281) near the phosphate cavity. The proximity to these residues and, in general, a complementarity with the binding site was also considered advantageous.
- if a peptide was able to produce more well-pointed binding positions, it was also considered an advantage. Since there were large differences in the raw numbers (as in the number of conformations generated) between the peptides, a "normalized" measure was calculated for a correct estimate, which was $N \leq (-7.5/N_{total})*100$, where $N \leq -7.5$ is the number of positions with a docking score of −7.5 or better, and $N_{total}$ is the total number of conformations. Table S2 contains these values (along with the number of "good" binding positions). It is noted that these results are not intended to rank the peptides, but rather represent a first filter for peptides that are capable of producing good binding positions.
- on the other hand, too many "weak contacts" as indicated on the Maestro interface or too close and collapsed structures were considered a disadvantage.

TABLE S2

Number and percentage of docking positions with a score better than -7.5 for shorter and modified peptides. pY represents phosphorylated tyrosine residues. Experimentally tested peptides are highlighted in italics.

| Peptide | N ≤ -7.5 | N ≤ -7.5/ Ntotal * 100 |
|---|---|---|
| Shorted peptides | | |
| NVpYG (SEQ ID NO: 35) | 463 | 8.5 |
| YNVpY (SEQ ID NO: 36) | 239 | 5.4 |
| GYNVpY (SEQ ID NO: 10) | 151 | 3.6 |
| GYNVpYG (SEQ ID NO: 33) | 128 | 3.4 |
| YNVpYG (SEQ ID NO: 34) | 86 | 3.1 |
| EGYNVpY (SEQ ID NO: 1) | 53 | 1.6 |
| EGYNVpYG (SEQ ID NO: 31) | 14 | 0.51 |
| Modified peptides | | |
| NTpYG (SEQ ID NO: 41) | 451 | 9.4 |
| NSpYG (SEQ ID NO: 43) | 247 | 9.0 |
| FVpYG (SEQ ID NO: 53) | 355 | 7.1 |
| YVpYG (SEQ ID NO: 49) | 282 | 6.7 |
| GYDVpYG (SEQ ID NO: 59) | 175 | 4.1 |
| FGYNDpYG (SEQ ID NO: 38) | 45 | 1.6 |
| FGYNVpYG (SEQ ID NO: 46) | 23 | 0.60 |
| YNKpY (SEQ ID NO: 39) | 10 | 0.36 |
| EGYNDpYG (SEQ ID NO: 61) | 6 | 0.26 |
| GYNVpYK (SEQ ID NO: 47) | 5 | 0.17 |
| FKYNVpYG (SEQ ID NO: 48) | 1 | 0.051 |

From the most promising peptides (based on the predicted binding poses), the inventors have generated a second ensemble of modified peptides. More specifically, the inventors have introduced modifications that is mutation or addition of amino acids in the positions where they would improve the secondary interactions with the STEP phosphatase. The modified peptides, along with the number of conformers are listed in Table S1. After docking to the STEP binding site, the inventors have used the same criteria to assess the docking poses, further adding that the peptide was to produce at least one binding pose where the residue is interacting with the STEP binding site, thus improving upon the original peptide.

Determination of the Interaction Constants for the Short p3Y-Derived Peptides and their Phosphomimetics with Inactive STEP32 Using Surface Plasmon Resonance (SPR) and Fluorescence Polarization The phosphopeptides predicted by molecular docking to have the most favorable docking poses with STEP were synthesized and used in experimental studies. The sequences of the peptides tested in the kinetic study are presented in Table 2.

For kinetic interaction studies by SPR, each of the short phosphopeptides was covalently immobilized on a flow cell of a carboxymethylated dextran chip. The peptides were linked N-terminally to a PEG2 spacer (H2N—CH2CH2OCH2CH2OCH2COOH) to provide mobility and allow their recognition and binding by the analyte protein STEP32. The amino group of the spacer was used to perform the covalent binding of the ligands to the sensor. In the case of the original p3Y peptide, used as positive control, the PEG spacer was not added but p3Y was immobilized via the c-amino group of the fourth lysine (K-4) of the peptide. At least five different concentrations of STEP32 C/S ranging between 100 nM and 500 μM were applied over each immobilized peptide in order to get detectable interaction signals.

Figure 4B:
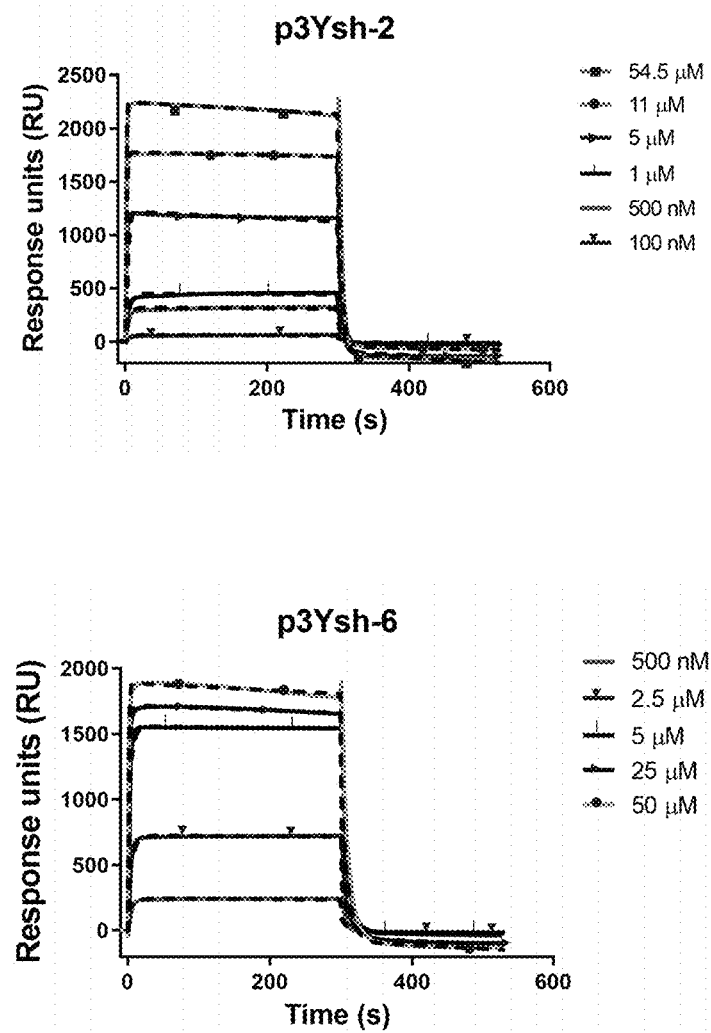
FIG. 4B—represents the analysis by surface plasmon resonance of the interaction between the 3Y-derived phosphopeptides p3Ysh-2, respectively p3Ysh-6 and STEP32 C/S. Surface plasmon resonance analysis of the interaction between the 3Y-derived phosphopeptides p3Ysh-2, respectively p3Ysh-6 and STEP32 C/S. Sensorgrams were obtained by injecting increasing concentrations of STEP32 on immobilized phosphopeptides. For each concentration of STEP32, signal obtained on control flow cell were subtracted from signal obtained on sample flow cell. Continuous lines represent measured binding curves and dotted lines represent fitted data for 1:1 kinetic.

Only four short peptides (p3Ysh-1, -2, -3, and -6) gave positive binding response on the sensorgram. The sensorgrams corresponding to the peptides p3Ysh-1, p3Ysh-3 and to the positive control peptide p3Y are presented in FIG. 5A, while the sensorgrams for p3Ysh-2 and p3Ysh-6 peptides are shown in FIG. 4B.

Sensorgrams were obtained by injecting increasing concentrations of STEP-32 onto the immobilized phosphopeptide. For each STEP32 concentration, the signal obtained on a control flow cell was subtracted from the signal obtained from a sample flow cell.

Figure 5A:
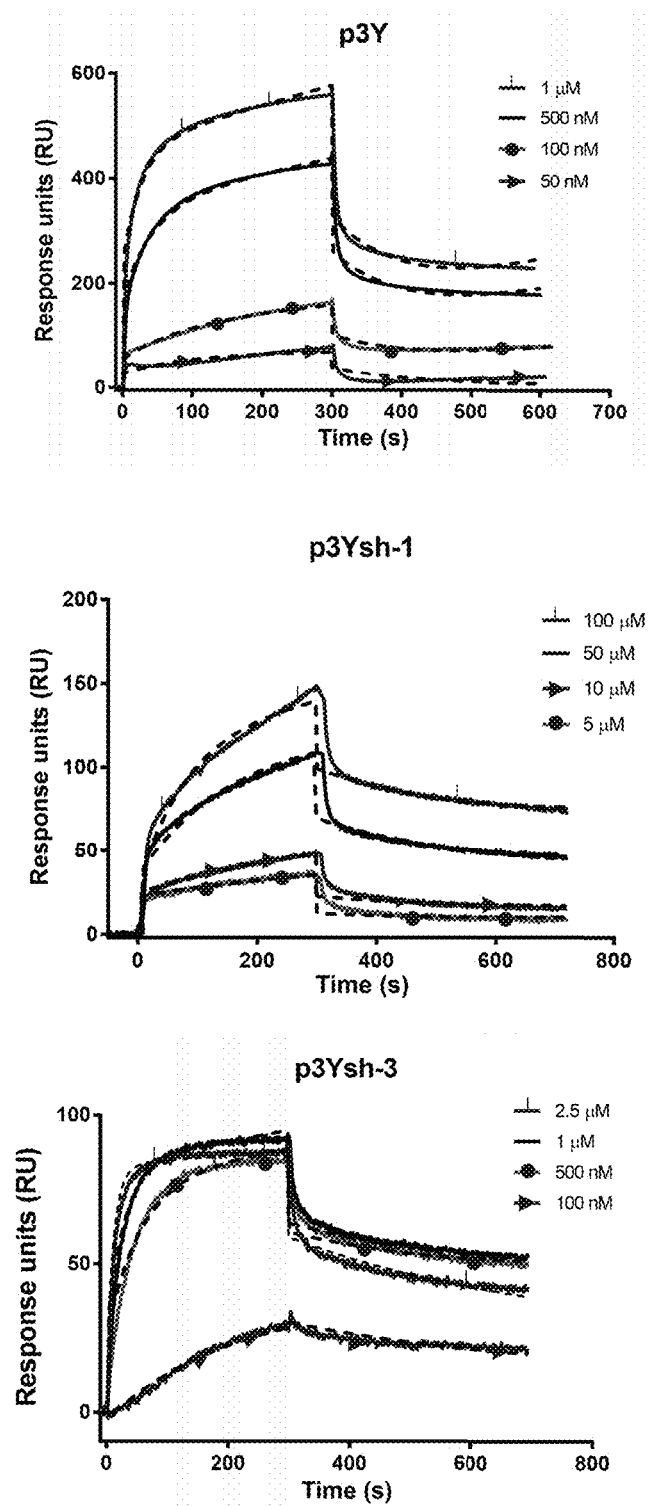
FIG. 5A—represents the analysis of the surface plasmon resonance of the interaction between the short p3Y-derived peptides and STEP32 C/S, obtained by injecting high concentrations of STEP32 on the immobilized phosphopeptides. Surface plasmon resonance analysis of the interaction between short p3Y-derived peptides and STEP32 C/S. Sensorgrams were obtained by injecting increasing concentrations of STEP32 on immobilized peptides. For each concentration of STEP32, signals obtained on control flow cell were subtracted from signals obtained on sample flow cell. Continuous lines represent measured binding curves and dotted lines represent 1:1 kinetic. Only the sensorgrams for three phosphopeptides are presented above: for the positive control peptide (p3Y), for the peptide with the lowest binding signal (p3Ysh-1) and for the peptide with the highest binding signal (p3Ysh-3).

With reference to FIG. 5A, only the sensorgrams for three phosphopeptides, respectively for the positive control peptide (p3Y), for the peptides with the lowest binding signal (p3Ysh-1) and for the peptides with the highest binding signal (p3Ysh-3) are presented.

The kinetic parameters obtained with the BIAevaluation program and the 1:1 Langmuir fit model are presented in Table S3.

TABLE S3

The summary of the kinetic data of the interaction between the 3Y-derived peptides and STEP32 C/S calculated using the BIAEvaluation program version 4.1.1. using a 1:1 Langmuir fit with a baseline deviation:

| phospho peptide | Peptide sequence | ka (1/Ms) | kd (1/s) | Ka (1/M) | Kd (μM) | Rmax (RU) |
|---|---|---|---|---|---|---|
| p3Y | ATYKEGY NVpYG (SEQ ID NO: 15) | 2.58E+04 | 5.99E-03 | 4.30E+06 | 2.32E-07 | 233 |
| p3Ysh-1 | PEG2- NVpYG (SEQ ID NO: 62) | 96.7 | 2.52E-03 | 3.84E+04 | 2.60E-05 | 103 |

TABLE S3-continued

The summary of the kinetic data of the interaction between the 3Y-derived peptides and STEP32 C/S calculated using the BIAEvaluation program version 4.1.1. using a 1:1 Langmuir fit with a baseline deviation:

| phospho peptide | Peptide sequence | ka (1/Ms) | kd (1/s) | Ka (1/M) | Kd (μM) | Rmax (RU) |
| --- | --- | --- | --- | --- | --- | --- |
| p3Ysh-2 | PEG2-YNVpYG (SEQ ID NO: 63) | 4.52E+04 | 0.179 | 2.53E+05 | 3.96E-06 | 2.02E+03 |
| p3Ysh-3 | PEG2-EGYNVpY (SEQ ID NO: 64) | 3.31E+04 | 1.76E-03 | 1.88E+07 | 5.31E-08 | 55.1 |
| p3Ysh-4 | PEG2-NSpYG (SEQ ID NO: 65) | — | — | No interaction | No interaction | — |
| p3Ysh-5 | PEG2-YVpYG (SEQ ID NO: 66) | — | — | ND | ND | — |
| p3Ysh-6 | PEG2-FGYNVpYG (SEQ ID NO: 67) | 1.79E+04 | 1.10E-01 | 1.63E+05 | 6.13E-06 | 1.39E+03 |
| p3Ysh-7 | PEG2-FSpYG (SEQ ID NO: 68) | — | — | No interaction | No interaction | — |
| 3Y-F2Pmp | ATYKEGYNV{F2Pmp}G (SEQ ID NO: 69) | 2.45E+04 | 6.56E-03 | 3.74E+06 | 2.68E-07 | 109 |
| 3Ysh-3-F2Pmp | EGYNV{F2Pmp} (SEQ ID NO: 70) | 1.99E+04 | 4.83E-03 | 4.12E+06 | 2.42E-07 | 83 |
| p-fin 4 | EGYNVpYE (SEQ ID NO: 2) | 7.82E+04 | 6.92E-03 | 1.13E+07 | 8.84E-08 | 73.8 |

The data obtained by SPR point out that the hexapeptide p3Ysh-3 binds to STEP32 C/S with the highest affinity, its equilibrium dissociation constant Kd being about 4 times lower than the Kd of the interaction between p3Y and STEP32 C/S. Other two peptides, p3Ysh-2 and p3Ysh-6 also bind the inactive mutant of STEP32, but less efficiently, their Kd values being about 17-and 6.4-times higher than the Kd of p3Y peptide.

The SPR analysis performed by the inventors showed that the phosphopeptide p3Ysh-3 binds to STEP32 C/S with a Kd of 60 nM, which reflects the highest affinity of all peptides, suggesting a high ability to prevent the interaction between GluA2 and STEP32.

In order to estimate the short peptides' capacity to dissociate the complex of STEP32 C/S with TAMRA-3Y-F2PmP a functional fluorescence polarization (FP) assay was used. The resulting experimental data were plotted on a curve (polarization vs competitor concentration). Characteristic for these curves is the IC50 value, i.e. the total competitor concentration at which half of the complex has been dissociated. This factor is used to calculate the inhibition constant, Ki for each interaction involving a competitor, STEP32 C/S and TAMRA-3Y-F2PmP. Ki is the indicator of the competitor's ability to dissociate the complex. Notably, the value of Ki is not the same as Kd, which was used to quantify the direct strength of the interaction between STEP32 and competitor (the short peptide), in the absence of a third component (p3Y peptide). The inventors carried out a set of FP-based experiments involving the same peptides studied by SPR and reported in the previous section as a means to evaluate those interaction data (Kd values). Above all, these experiments provided information on the peptides p3Ysh-4, -5, and -7 for which the interaction could not be detected by SPR.

Figure 6A:
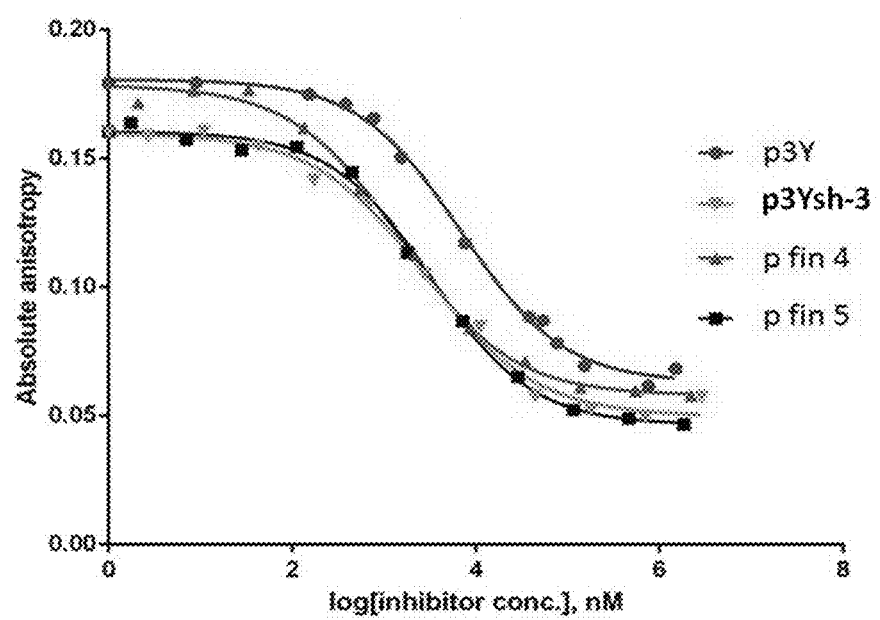
FIG. 6A—represents the curves of the data obtained by fluorescence polarization measurements for the study of the inhibition of the interaction STEP32-TAMRA-3Y-F2Pmp with p3Y-derived peptides. Data processing for the inhibition of STEP32-TAMRA-3Y-F2Pmp interaction of p3Y-derived peptides by fluorescence polarization. Inhibition curves of the three most efficient phosphopeptides, p3Ysh-3, p-fin4 and p-fin5 and the standard 3Y-P (ATYKEGYNVpYG, SEQ ID NO: 15) are plotted for comparison. The lowest IC50 value is obtained for p-fin 4 (see Table 3).

The results shown in FIG. 6A illustrate the capacity of the strongest competitors to disrupt the complex between STEP32 C/S and TAMRA-3Y-F2PmP. The inhibition curves of the three most effective phosphopeptides, p3Ysh-3, p-fin4 and p-fin5 and standard 3Y-P (ATYKEGYNVpYG (SEQ ID NO: 15)) are plotted for comparison. The lowest IC50 value was obtained for p-fin 4, as seen in Table 3.

These results suggest that the p3Ysh-3 peptide is the strongest competitor, having a lower Ki, i.e. a better or at least a similar capacity to p3Y to dissociate the STEP-p3Y complex. Eventually, two sets of data were generated, the first one using SPR and yielding Kd (data taken from Table S3) and the second using FP and yielding K values. The results are summarized in Table 2.

TABLE 2

Comparative table for FP and SPR measurements of p3Y-derived peptides.
$K_i$ values are obtained by FP measurements and $K_d$ values are obtained by SPR measurements.

| phosphopeptide | peptide sequence | $K_i$ (µM) | $K_d$ (µM) |
|---|---|---|---|
| p3Ysh-1 | PEG2-NVpYG (SEQ ID NO: 62) | 4.99 | 26 |
| p3Ysh-2 | PEG2-YNVpYG (SEQ ID NO: 63) | 13.13 | 3.96 |
| p3Ysh-3 | PEG2-EGYNVpY (SEQ ID NO: 64) | 1.64 | 0.06 |
| p3Ysh-4 | PEG2-NSpYG (SEQ ID NO: 65) | 13.67 | No interaction |
| p3Ysh-5 | PEG2-YVpYG (SEQ ID NO: 66) | 5.34 | ND |
| p3Ysh-6 | PEG2-FGYNVpYG (SEQ ID NO: 67) | 6.96 | 6.13 |
| p3Ysh-7 | PEG2-FSpYG (SEQ ID NO: 68) | 4.57 | No interaction |
| p3Y | ATYKEGYNVpYG (SEQ ID NO: 15) | 2.36 | 0.24 |

Further Optimization of p3Y-Peptide Derivatives and their In Vitro Testing

According to Table 2, the tyrosine-phosphorylated peptides p3Ysh-3 as well as p3Y (ATYKEGYNVpYG (SEQ ID NO: 15)) performed the best regarding their ability to dissociate the STEP-peptide complexes. Remarkably, the Kd value corresponding to the hexapeptide is more than twice smaller than the Kd of p3Y, meaning that a much shorter version of p3Y has an even better disrupting capacity than p3Y.

Regarding the ligand efficiency (LE) [37], the first round of LE optimization significantly improved the LE of the starting point, which is p3Y.

Thus, LE(p3Y)=0.38 vs. LE(p3Ysh-3)=0.64). As a part of efforts to further optimize the ligand efficiency, the inventors have carried out a second round of optimization, based directly on the best EGYNVpY (SEQ ID NO: 1) candidate, testing a few specific hypotheses proposed during computational modeling.

First, in addition to identifying EGYNVpY (SEQ ID NO: 1) as the best candidate, the results also hint the importance of the first glutamate residue of this peptide (E871 in GluA2), since the peptides in which this residue was mutated or omitted have shown deteriorated $K_i$ and $K_d$ values, as per Table 2.

Figure 5B:
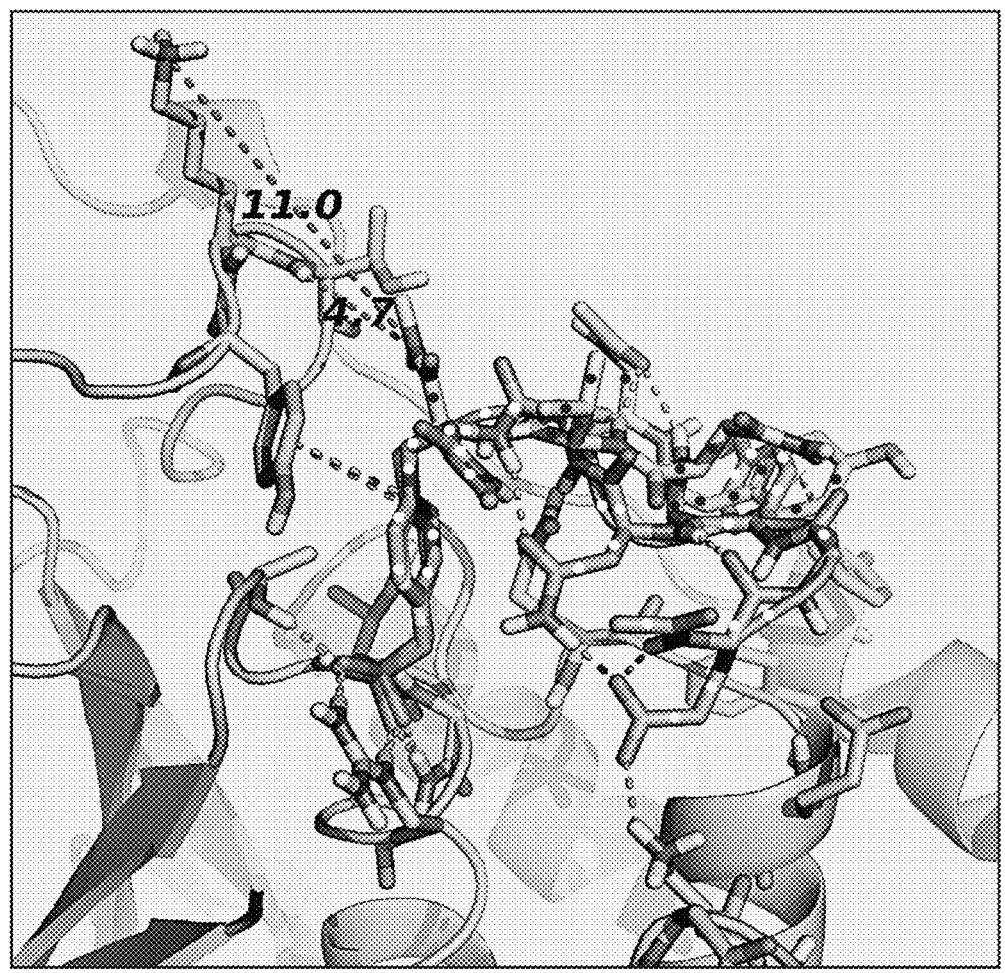
FIG. 5B—represents the overlapping binding positions of EGYNVpY (SEQ ID NO: 1) and GYNVpY (SEQ ID NO: 10) peptides. Overlaid binding poses of the peptides EGYNVpY (SEQ ID NO: 1, the white dotted chain) and GYNVpY (SEQ ID NO: 10, black dotted chain). The interaction pattern of the two peptides with STEP are quite similar (including the interaction with the phosphate cradle and the π-π stacking with the tyrosine residues Y281 and Y304). On the other hand, the salt bridge between EGYNVpY (SEQ ID NO: 1) and the K439 residue of STEP (bottom of image) is highly important for stabilizing the protein-peptide complex, as verified by the experimental results.

As shown in FIG. 5B, docking the two peptides to the STEP binding site reveals similar binding modes with the notable salt bridge between the first glutamate residue of EGYNVpY (SEQ ID NO: 1) and K439 of STEP, suggested as a further stabilizing interaction for the complex. This advantage was confirmed by fluorescence polarization, where the deletion or even a minor modification of the glutamate residue (to Q or N) caused a deterioration of the inhibition constant, as well as the $IC_{50}$ value (Table 3).

Figure 6B:
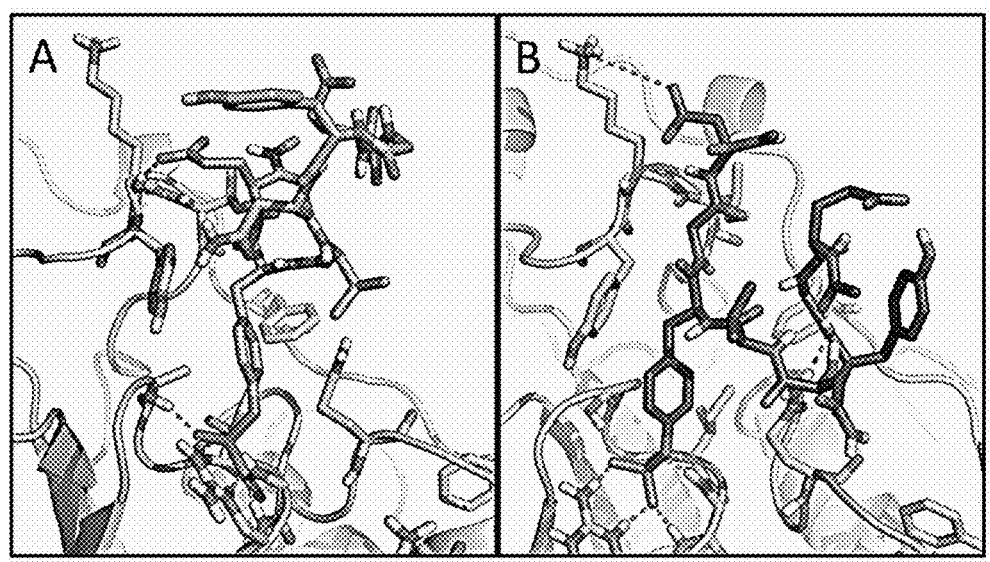
FIG. 6B—represents the docked positions of the derivatives of EGYNVpY (SEQ ID NO: 1). (A) The EGYNVpYE (SEQ ID NO: 2) peptide forms an additional hydrogen bond with the secondary cavity. (B) The EGYNVpYGD (SEQ ID NO: 3) peptide forms a saline bridge with the side chain of K439, while maintaining the secondary interaction with Q516. Docked poses of EGYNVpY (SEQ ID NO: 1) derivatives. (A) The EGYNVpYE (SEQ ID NO: 2) peptide establishes an additional hydrogen bond with the secondary cradle. (B) The EGYNVpYGD (SEQ ID NO: 3) peptide establishes a salt bridge with the sidechain of K439, while maintaining the secondary interaction with Q516.

Secondly, the predicted binding mode of EGYNVpY (SEQ ID NO: 1) reveals that the "secondary cradle", formed by the backbone amines and side chain residues OH of the radicals K305 and T306 (which are generally accepted as selectivity-determining residues) could be targeted by adding an appropriate acidic residue to the C terminus of the hexapeptide. Therefore, the inventors proposed two such EGYNVpY (SEQ ID NO: 1) derivatives by docking and visual inspection: EGYNVpYE (SEQ ID NO: 2) and EGYNVpYGD (SEQ ID NO: 3), having the binding configurations of FIG. 6B. Of the two peptides, the inhibitory activity of EGYNVpYGD (SEQ ID NO: 3) is comparable to EGYNVpY (SEQ ID NO: 1), while EGYNVpYE (SEQ ID NO: 2) presents about two-fold improvement over the original hexapeptide in terms of its inhibition constant (Table 3).

Gathering all information so far obtained, five phosphopeptides were synthesized and further tested by FP to determine their capacities to dissociate STEP-GluA2 complex. The results obtained are listed in Table 3.

TABLE 3

Results of the inhibitory effect of the final 3Y-derived peptides on the TAM-3Y-F2Pmp-STEP32 complex, obtained by FP.

| Name | Sequence | $K_i$ [µM] | $IC_{50}$ [µM] |
|---|---|---|---|
| p-fin 1 | GYNVpY (SEQ ID NO: 10) | 1.9 | 8.01 |
| p-fin 2 | DGYNVpY (SEQ ID NO: 71) | 1.85 | 7.15 |
| p-fin 3 | NGYNVpY (SEQ ID NO: 72) | 2.16 | 8.84 |
| p-fin 4 | EGYNVpYE (SEQ ID NO: 2) | 0.36 | 1.86 |
| p-fin 5 | EGYNVpYGD (SEQ ID NO: 3) | 0.76 | 3.36 |
| p3Ysh-3 | PEG2-EGYNVpY (SEQ ID NO: 64) | 0.69 | 2.60 |

The inventors used PEG2-EGYNVpY (SEQ ID NO: 64) instead of EGYNVpY (SEQ ID NO: 1) in order to correlate the results from the previous round of experiments (Table 2). Clearly, the phospho-hexapeptide PEG2-EGYNVpY (SEQ ID NO: 64) and the phospho-heptapeptide EGYNVpYE (SEQ ID NO: 2) were the most efficient in dissociating the complexes, thus confirming the docking predictions.

Therefore, the inventors further selected both the hexapeptide and the heptapeptide for in vivo studies, for animal behavior experiments using the phosphorylated form of these peptides.

Prior to in vivo studies, the inventors determined the inhibition constant for the interaction of each peptide (p3Y, EGYNVpY (SEQ ID NO: 1) and EGYNVpYE (SEQ ID NO: 2)) with STEP32. The results obtained are presented in Tables 2 and 3.

Figure 7:
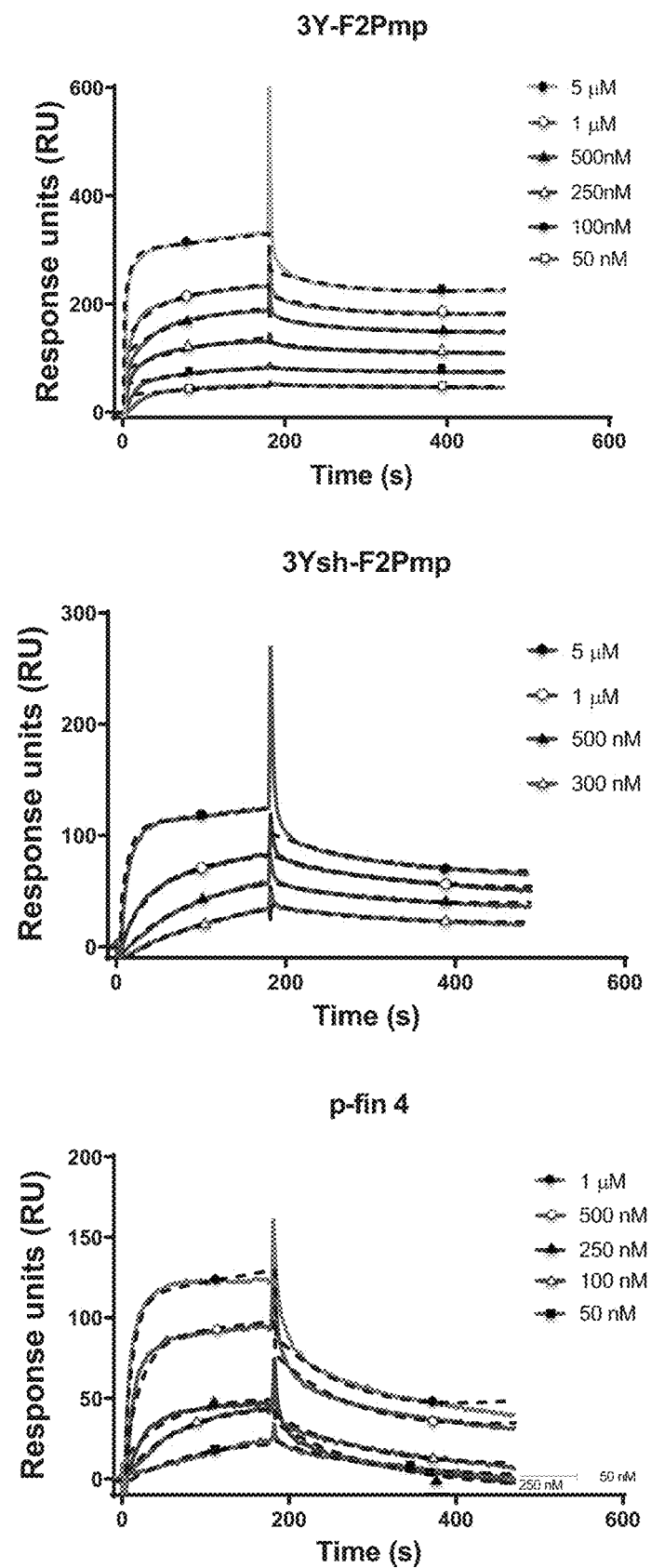
FIG. 7—represents the analysis by surface plasmon resonance of the interaction between STEP32 and phosphorylated tyrosine and the peptides containing F2Pmp. Surface plasmon resonance analysis of the interaction between STEP32 and the tyrosine-phosphorylated and F2Pmp-containing peptides selected for electrophysiological studies. For the immobilized 3Y-F2Pmp and 3Ysh-F2Pmp phosphomimetic peptides, STEP32 WT was used as the analyte whereas for p-fin 4 heptapeptide, STEP32 C/S mutant was used. At least four concentrations of STEP32 were injected over the peptides immobilized on the sensor chip. Binding curves were obtained by subtracting the signal obtained on control flow cell from the signal obtained on sample flow cell. Continuous lines represent measured binding curves and dotted lines represent 1:1 kinetic fit.

Table 4 and FIG. 7 show the results measured by SPR of the binding strength for the binding of some of the peptides and peptidomimetics of the present invention to STEP32, strength reflected in the value of the dissociation constant Kd.

TABLE 4

Comparative binding affinities of tyrosine-phosphorylated and F2Pmp-containing peptides, determined by SPR:

| Name | Sequence | $K_d$ (µM) |
|---|---|---|
| 3Y | ATYKEGYNVYG (SEQ ID NO: 73) | not measured |
| 3Y-F2Pmp | ATYKEGYNV{F2Pmp}G (SEQ ID NO: 69) | 0.27 |
| 3Ysh-3-F2Pmp | EGYNV{F2Pmp} (SEQ ID NO: 70) | 0.24 |
| fin4-F2Pmp | EGYNV{F2Pmp}E (SEQ ID NO: 74) | not measured |
| p-fin 4 | EGYNVpYE (SEQ ID NO: 2) | 0.09 |

These results show that tyrosine-phosphorylated or phosphonomimetic derivatives of 3Y peptides, 3Ysh-3-F2Pmp and p-fin4 bind tightly to STEP32 having $K_d$ values in the submicromolar range. This finding suggests these peptides could efficiently disrupt STE32-GluA2-CT complex, thus preventing AMPAR internalization. Moreover, peptides 3Ysh-3-F2Pmp and p-fin4 bind STEP32 comparably or even tighter than 3Y (the peptide derived from GluA2-CT).

In particular, said interference peptide is used:
  in the prevention and treatment of depression and anxiety,
  in the prevention and treatment of neuro-degenerative diseases, such as but not limited to Alzheimer's disease or Parkinson's disease,
  in the prevention and treatment of both depression and anxiety and neuro-degenerative conditions, such as but not limited to Alzheimer's disease or Parkinson's disease.

The In Vivo Effect of the Peptides on Working-, Short Term- and Long Term Memory The above findings recommend all the peptides according to the invention and first of all the p-fin4 peptide as a potential cognitive enhancer.

For this reason, a second object of the invention is a peptidic compound that includes a phosphorylated interference peptide coupled with an amino acid sequence called transport sequence, capable of penetrating the cell membrane of the neurons.

The viral amino acid sequence GRKKRRQRRRPQ (SEQ ID NO: 75), generically designated as Tat, was chosen as transport sequence in an embodiment of the invention.

The respective peptidic compound according to the invention is to be used as drug (?).
  Particularly, the respective compound is to be used:
  in the prevention and treatment of depression and anxiety
  in the prevention and treatment of neuro-degenerative diseases, such as, but not limited to, Alzheimer's disease or Parkinson's disease
  in the prevention and treatment of depression and anxiety as well as that of neuro-degenerative diseases, such as, but not limited to, Alzheimer's disease or Parkinson's disease.

In the above-mentioned peptidic compound, the interference peptide is either EGYNVpY (SEQ ID NO: 1) or EGYNVpYE (SEQ ID NO: 2).

To confirm the cognitive enhancing potential of the peptide compound comprising a phosphorylated interference peptide according to the invention, coupled with a Tat sequence, the inventors performed memory tests using a scopolamine-induced cognitive impairment model in rats.

Scopolamine is frequently used to study various forms of dementia since it can induce memory and cognitive deficits. Numerous neurobehavioral studies have demonstrated that scopolamine can impair various forms of memory (particularly short-term memory) and learning, both in humans and rodents [38]. It was shown that chronic scopolamine administration in rats reduces the performance in radial maze tasks involving working memory [39]. Thus, the inventors have analyzed the effects of peptides 3Y, p3Y, p3Ysh-3 and p-fin4, both on short- and on long term memory, in rat scopolamine-induced model, using the eight-arm radial maze and Y-maze. All of the tested peptides, that is 3Y, p3Y, p3Ysh-3 and p-fin4, have been N-terminally fused to the TAT cell-penetrating sequence.

Effects on the Short-Term Memory (Working Memory)

Figure 8:
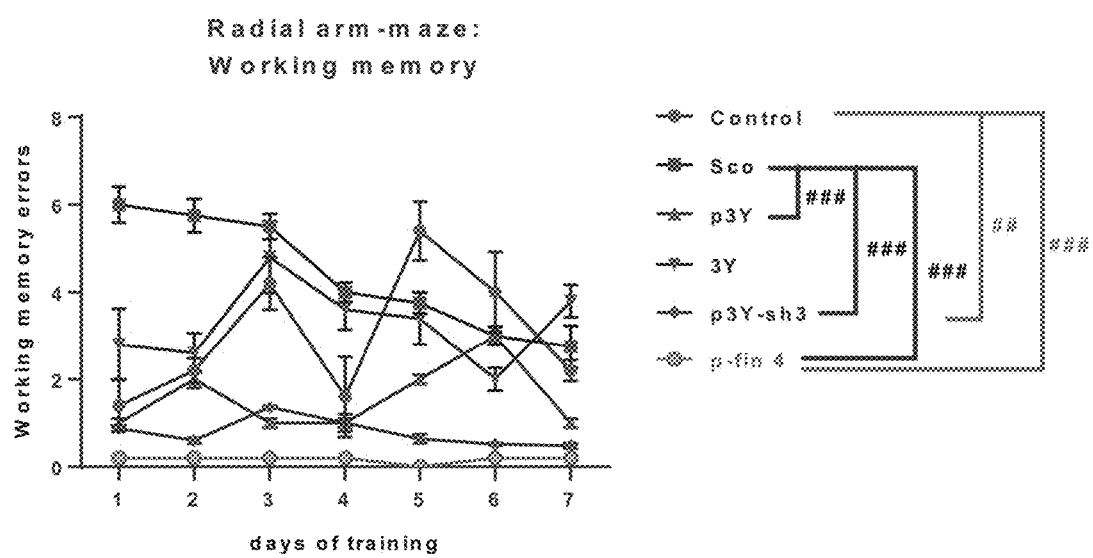
FIG. 8—represents the effects of peptide administration (15 µM) in rats previously treated with scopolamine (Sco −0.7 mg/kg) on the number of working memory errors (short-term) in the maze with radial arms. Effects of peptide administration (15 µM) on the number of working memory errors within the radial arm maze test in the scopolamine (0.7 mg/kg)-treated rats (Sco). Values are mean±S.E.M (n=5). For Tukey's post hoc multiple comparison test: Sco vs. (TAT-) p3Y: ###$p<0.0001$; Sco vs. (TAT-)p3Y-sh3: ###$p<0.0001$ and Sco vs. (TAT-)p-fin 4: ###$p<0.0001$. 5 adult male rats were used for each treatment group.

Scopolamine injection significantly increased the number of working memory errors (FIG. 8), as compared with the control group (p<0.0001), suggesting a memory impairment profile. All peptide administration, but especially (TAT-) p3Y, (TAT-)p3Y-sh3, and (TAT-)p-fin 4, showed a significant reduction in the number of working memory errors increased by scopolamine, as compared to scopolamine-alone treated rats (p<0.0001).

Figure 9:
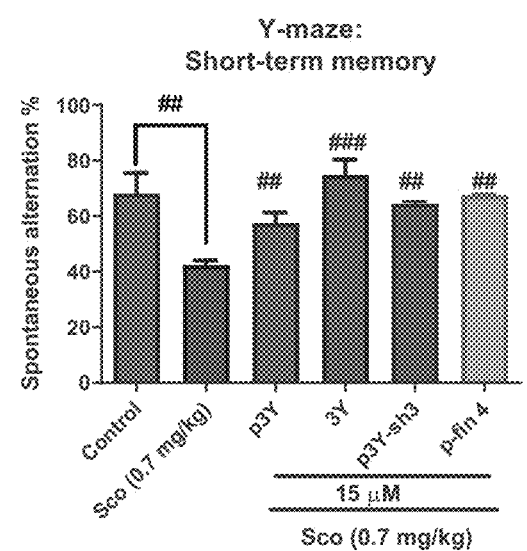
FIG. 9—represents the way in which the administration of peptides (15 µM) reversed the deficiency caused by scopolamine (Sco, 0.7 mg/kg) in the percentage of spontaneous alternations in the Y-maze. The peptide administration (15 µM) reversed scopolamine (Sco, 0.7 mg/kg)-induced deficits on the spontaneous alternation percentage within the Y-maze. Values are mean±S.E.M (n=5). For Tukey's post hoc multiple comparison test: Sco vs. (TAT-)p3Y: ##$p<0.001$; Sco vs. (TAT-)3Y: ###$p<0.0001$; Sco vs. (TAT-)p3Y-sh3: ##$p<0.001$ and Sco vs.(TAT-)p-fin4: ##$p<0.001$.

Scopolamine injection significantly decreased short-term memory performance within the Y-maze test, as evidenced by a significant decrease of the spontaneous alternation percentage compared with the control group (p<0.0001). Peptide administration, but especially (TAT-)3Y administration, significantly ameliorated the spontaneous alternation percentage (p<0.0001) decreased by scopolamine, as compared to scopolamine alone-treated rats (FIG. 9). The investigated peptides ((TAT)-3Y, (TAT-)p3Y, (TAT-)p3Y-sh3 i (TAT-)p-fin 4) successfully countered the effect of scopolamine on working-memory in the Y-maze and in the eight-arm maze test. This result is consistent with several factors. First, scopolamine administration results in reduced GluA2 expression [41]. A decrease in GluA2 expression leads to impaired working memory [42]. On the other hand, one should keep in mind that the disruption of STEP-GluA2-CT interaction inhibits AMPAR internalization and consequently reduces LTD expression. Indeed, mice lacking STEP61 exhibit enhanced hippocampal memory in the Morris water maze and in a radial-arm water maze [43]. These correlated facts suggest that the improved working memory performance observed in the Y-maze and in the eight-arm radial maze tests is due to the inhibition of the GluA2-STEP61 interaction via interference peptides and rescue of the receptor from internalization.

Effects on the Long Term Memory (Reference Memory)

Figure 10:
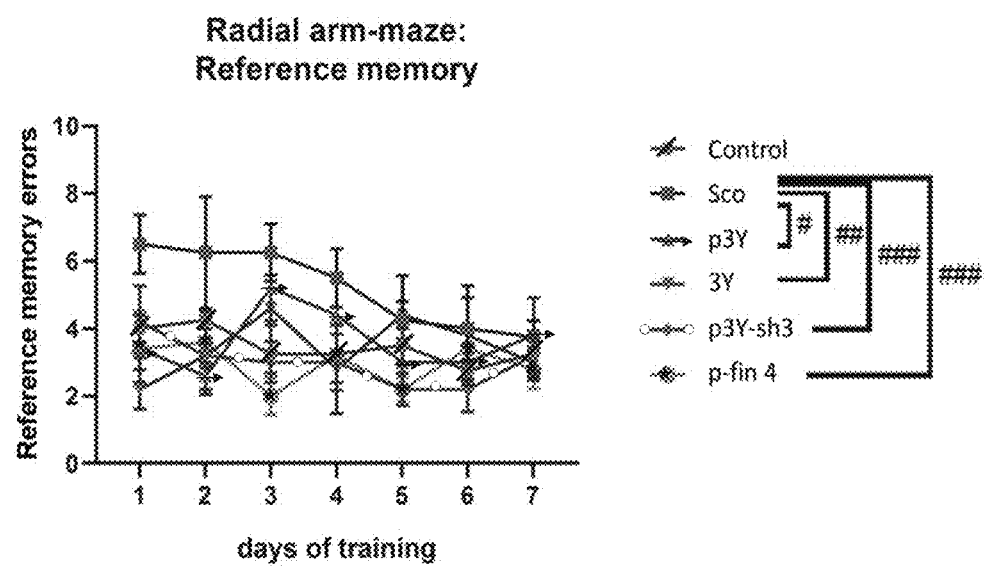
FIG. 10—represents the effects of peptide administration (15 µM) in rats previously treated with scopolamine (Sco −0.7 mg/kg) on the number of reference (long-term) memory errors in the maze with radial arms. Effects of peptide administration (15 µM) on the number of reference memory errors within the radial arm-maze test in the scopolamine (0.7 mg/kg)-treated rats. Values are mean±S.E.M (n=5). For Tukey's post hoc multiple comparison test: Sco vs. (TAT-)p3Y: #$p<0.01$; Sco vs. (TAT-)3Y: ##$p<0.001$, Sco vs. (TAT-)p3Y-sh3: ###$p<0.0001$, and Sco vs. (TAT-)p-fin 4: ###$p<0.0001$.

Scopolamine injection significantly increased the number of reference memory errors (FIG. 10), as compared with the control group (p<0.001), suggesting a reference memory impairment profile.

Administration of peptides, but especially (TAT-)p3Y-sh3 and (TAT-)p-fin 4, showed a significant reduction in the number of reference memory errors increased by scopolamine, as compared to scopolamine-alone treated rats (p<0.0001).

The In Vivo Effect of Peptides on Depression and Anxiety

In order to examine the possible antidepressant-like effect of the peptides, the inventors subjected the rats to forced swim test (FST) and elevated plus maze test (EPMT)

Forced Swim Test

Figure 11:
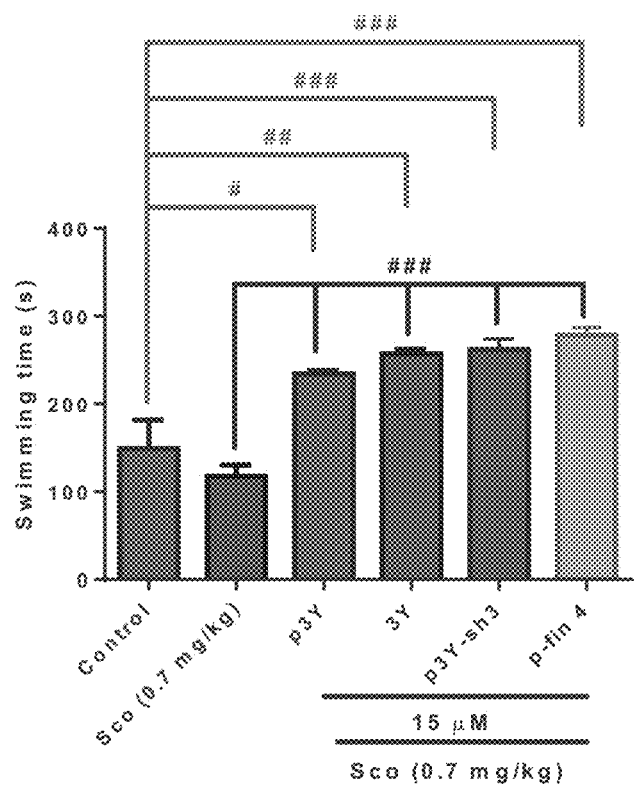
FIG. 11—represents the antidepressant effect of peptides (15 µM) on swimming time in the forced swimming test in rats treated with scopolamine (0.7 mg/kg). The antidepressant effect of the peptides (15 µM) on the swimming time within the forced swimming test in the scopolamine (0.7 mg/kg)-treated rats. Values are mean±S.E.M (n=5). For Tukey's post hoc multiple comparison test: Sco vs. (TAT-) p3Y: ###$p<0.0001$; Sco vs. (TAT-)3Y: ###$p<0.0001$, Sco vs. (TAT-)p3Y-sh3: ###$p<0.0001$ and Sco vs. (TAT-)p-fin4: ###$p<0.0001$.

As shown in FIG. 11, the animals treated with Scopolamine displayed a significant decrease of the swimming time compared to the control group (p<0.01). Furthermore, when treated with the peptide-compounds according to the invention, the scopolamine-treated animals exhibited substantially increased swimming time as compared to the control group (p<0.0001), suggesting that all four peptides display an antidepressant-like effect.

Figure 12:
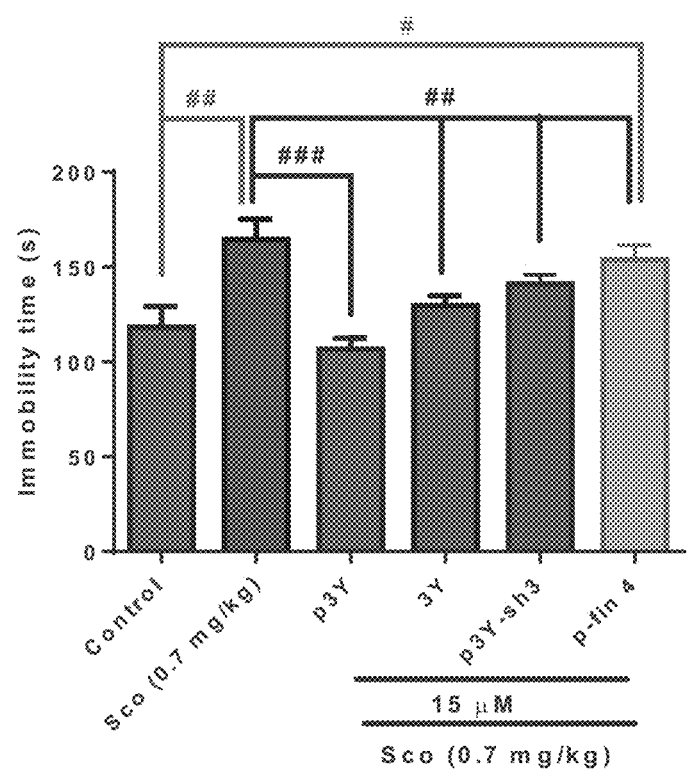
FIG. 12—represents the antidepressant effect of peptides (15 µM) on immobility time in the forced swimming test in rats treated with scopolamine (0.7 mg/kg). The antidepressant effect of the peptide (15 µM) on the immobility time within the forced swimming test in the Sco (0.7 mg/kg)-treated rats. Values are mean±S.E.M (n=5). For Tukey's post hoc multiple comparison test: Sco vs. (TAT-)p3Y.

Also, as shown in FIG. 12, the rats treated with Scopolamine showed high levels of the immobility time compared to the control group (p<0.001), indicating high levels of depression. The administration of peptides induced a significant decline of the immobility time (p<0.001), especially (TAT-)p3Y, suggesting again an antidepressant-like activity.

Elevated Plus Maze Test

As shown in FIG. 13, the percentage of time spent by Scopolamine-treated animals in the open arms was significantly reduced as compared to the control group (p<0.0001). Reducing the time spent in the open arms suggests high levels of anxiety in scopolamine-treated rats. By contrast, all groups treated with peptides, but especially (TAT-)p3Y-sh3 and (TAT-)p-fin4, showed high percentage of the open arms time as compared to scopolamine-alone treated rats (p<0.0001), indicating an anxiolytic profile.

As observed in FIG. 14, the number of entries in the open arms performed by the Sco-treated animals was significantly reduced as compared to the control group (p<0.0001). Reducing the number of entries in the open arms suggests high levels of anxiety in Sco-treated rats. Furthermore, all peptides, but especially (TAT-)p3Y-sh3 and (TAT-)p-fin4, correlated to a high number of entries in the open arms as compared to Sco-alone treated rats (p<0.001), clearly indicating an anxiolytic effect.

Scopolamine-induced anxiety in rats, in elevated-plus maze experiments has been since longtime reported [44]. A mechanism in which scopolamine blocks cholinergic signaling both directly, as an muscarinic acetylcholine receptor mAChR antagonist and indirectly, by stimulating ACh esterase (AChE) is considered responsible for the observed effect [45],[46]. Acute stress has been shown to increase ACh levels in the hippocampus and seems to involve hyperexcitability of the cholinergic system and even provoke LTP in some regions of the hippocampus [48], [49], [50]. On the other hand, hippocampal LTD suppresses the development of anxiety behaviours in response to stress [51]. In line with this mechanism, inhibiting LTD through injection of 3Y peptides should enhance the anxiety-like behaviour. Indeed, confirming that synaptic AMPA expression promotes anxiety, mice injected with 3Y spent more time immobile in a social conflict experiment, while displaying increased latency in approaching a previously learned food reward when offered in a novel environment [51].

In opposition to the effects reported in the state of the art, the inventors' experiments on rats in the elevated plus maze indicate an anxiolytic effect on the animals injected with AMPAR endocytosis-blocking peptides.

Evaluation of the Peptides Optimized in Interaction with BRAG2

Docking the non-phosphorylated versions of the three most important short peptides (EGYNVY (SEQ ID NO: 4), EGYNVYGD (SEQ ID NO: 6) and EGYNVYE (SEQ ID NO: 5)) to the proposed BRAG2 binding site (similar to the methodology described in Example 9) revealed favorable binding modes, which have secondary interactions with the most important interactive residues above-identified for BRAG2, namely the tyrosine binding subpocket and the two grooves behind the binding site. Here, the words "subpocket" and "groove" reflect a difference of shape: the word "subpocket" is used for small, cavern-like binding sites, and the word "groove" is used for more open, channel-like binding sites, where the peptide can be sandwiched between different parts of the target protein. With reference to FIG. 15, additional ionic interactions are observed between the negatively charged side chains R402, R444 and R630 of BRAG2.

These results support the dual inhibitor quality of the respective phosphopeptides EGYNVpY (SEQ ID NO: 1), EGYNVpYE (SEQ ID NO: 2), EGYNVpYGD (SEQ ID NO: 3): (i) targeting STEP phosphatase in phosphorylated form and (ii) after dephosphorylation by STEP, targeting BRAG2 in dephosphorylated form of peptides.

Examples of Preparation

The present invention, as described above, will be more readily understood by reference to the following examples of preparation and animal testing, which provide a way to illustrate it without the intention of limiting it.

The experiments below are not the only experiments performed by the inventors, therefore they reserve the right to complete them in accordance with the law.

All animal testing procedures have complied with European Regulations on the protection of animals used for scientific purposes (Directive 2010/63/EU).

Example 1—GST-GluA2 Expression and Purification

The plasmid pGEX-6P1-GST-GluA2 containing the C-terminal region of human GluA2 (aa. 834-883 from AMPA receptor) N-terminally fused with a GST-tag was transformed in *E. coli* BL21 strain. Protein expression was induced with 1 mM IPTG for 3 hours at 37° C. Bacterial cells were resuspended in PBS 1×(NaCl 140 mM, KCl 2.7 mM, $Na_2HPO_4$ 10 mM, $KH_2PO_4$ 1.8 mM pH=7.34) with 0.1% NP-40, 1 mM EDTA, 2 mM DTT, 1 mM PMSF and lysed using a French press (Thermo). The lysate was clarified by centrifugation 30 min at 40000×g, 4° C. The resulting supernatant was loaded on a GSTrap FF 5 ml column (GE Healthcare) and eluted with 0-20 mM reduced glutathione (GSH). The purification was performed using a FPLC AEKTA system (GE Healthcare™). Fractions collected were analyzed by SDS-PAGE. Collected fractions were dialyzed against a buffer containing 50 mM Tris, 150 mM NaCl, 1 mM EDTA, 1 mM DTT 1 mM, pH=7.5. Finally, the purified protein was stored in small aliquots and at −80° C.

Example 2—STEP32 Expression and Purification

For STEP32 WT and the C/S substrate trapping mutant expression pLIC-SGC1-PTPN5 WT (access no. 39166, Addgene™), respectively pLIC-SGC1-PTPN5 C496S (access no. 38887, Addgene™) constructs containing the catalytic domain of protein tyrosine phosphatase STEP/PTPN5 (aa. 282-563) N-terminally fused with a 6×His-tag (SEQ ID NO: 76) were transformed into *E. coli* BL21(DE3) bacterial strain. Proteins expression was induced with 1 mM IPTG overnight (~16 h) at 18° C. The resulting precipitate was resuspended in lysis buffer (50 mM HEPES, pH7.5, 10 mM imidazole, 500 mM NaCl, 5 mM β-mercaptoethanol, 0.5 mg/mL lysozyme, UltraCruz™ protein inhibitor cocktail tablets as specified by the manufacturer) and lysed using a French press (Thermo™). The lysate was cleared by centrifugation at 40000×g and 4° C. for 30 min, filtered on a 0.22 µm membrane filter and then applied on a HisTrap™ HP 5 ml Ni-Sepharose column. The elution was carried out using a gradient elution with elution buffer (50 mM HEPES, pH 7.5, 250 mM imidazole, 500 mM NaCl, 5 mM (3-mercaptoethanol), 0 to 100% over 25 min at a 2 ml/min flow. Fractions were collected and evaluated by SDS-PAGE. Collected fractions were dialyzed against a buffer containing 50 mM HEPES, pH 7.4, 500 mM NaCl, 1 mM DTT. Finally, the purified proteins were divided in small aliquots and stored at −80° C. with 10% glycerol.

Example 3—Peptides Design

Peptides used in this study were synthesized by GenScript Biotech™ (USA) and Biomatik™ (USA). The "Ala-scan peptides" were obtained by replacing each amino acid from the sequence of the 3Y peptide (excepting the essential pY876) with an alanine. Next, a virtual peptide library was generated by a docking study of GluA2-CT derivative into the binding site of the STEP PDB-structure (2CJZ) and seven peptides with the most favorable docking scores, named "short 3Y-derived peptides", were selected for further binding experiments. The short 3Y-derived peptides were synthesized to contain an N-terminally PEG2 spacer ($H_2N$—$CH_2CH_2OCH_2CH_2OCH_2COOH$) to ensure their flexibility and accessibility to the catalytic domain of STEP. For the study of peptidomimetic compounds, the p3Y peptide, ATYKEGYNVpYG (SEQ ID NO: 15) and the hexapeptide p3Ysh-3, EGYNVpY (SEQ ID NO: 1), were modified so that the essential phosphotyrosine Y876 was replaced with phosphonodifluoromethyl phenylalanine (F2Pmp), a non-hydrolysable mimetic phosphotyrosine. Peptides 3Y, p3Y, p3Ysh-3 and p-fin4 (EGYNVpYE (SEQ ID NO: 2)) used in the behavioral experiments were N-terminally fused to the TAT sequence whose role is to overcome the lipophilic barrier of the cellular membranes.

Example 4—Tyrosine Phosphorylation of GST-GluA2

The purified GST-GluA2 was submitted to in vitro phosphorylation in the presence of the active Src protein (14-326, Merck™) and ATP, for 1 h at 25° C. All reactions were carried out in kinase assay buffer (20 mM MES pH 6.5, 150 mM NaCl, 10 mM $MgCl_2$, 1mMDTT). A reaction containing GST-GluA2 but without Src kinase was carried out as a negative control. Tyrosine phosphorylation of GST-GluA2 was checked by western blotting using anti-pTyr antibody (PY99) HRP (sc-7020 HRP, Santa Cruz Biotechnology™). Then, the membranes were reprobed with anti-GST antibodies (G7781, Sigma-Aldrich™)

Example 5—GST-GluA2—STEP32 Pulldown

In order to demonstrate the capacity of p3Y, p3Y-sh3 and p-fin4 to inhibit the formation of the GluA2-STEP32 complex, phosphorylated GST-GluA2 (57 µg) was pulled down using GSH Sepharose beads (20 µl). Prior to binding and after contacting the beads with phosphorylated GST-GluA2, the beads were washed thoroughly with interaction buffer (25 mM HEPES, 150 mM NaCl, 1 mM MgCl2, 1% Triton™ X-100, 1 mM DTT, pH=7.5). Triton™ X-100 was used to avoid nonspecific binding and to minimize the risk of precipitation for any of the proteins. Subsequently, the beads are put in contact with solutions containing STEP32 C/S and several concentrations of p3Y (yielding concentrations of 1000 µM, 100 µM, 10 µM, 1 µM in the solution in contact with the beads). Beads were washed twice with wash buffer to remove excess STEP32 C/S. Results were analyzed using SDS-PAGE (FIG. 2A). These results indicate that p3Y is capable of disrupting the GST-GluA2-STEP32 C/S complex in a dose-dependent manner. In a subsequent setup, peptides p3Y, p3Y-sh3 and p-fin4 were compared in their ability to disrupt the above-mentioned complex, using western blot (FIGS. 2B and 2C). From these latter experiments one can conclude that TAT-p-fin4 has the strongest inhibitory effect on the formation of the GST-GluA2-STEP32 C/S complex (Western blotting performed using the 6×His tag (SEQ ID NO: 76) on the STEP32 C/S).

Example 6

In Example 5 it was shown that the TAT-phosphopeptides TAT-p3Y, TAT-p3Y-sh3 and TAT-p-fin4 proved to significantly inhibit the interaction of the C-terminal region of GluA2 with STEP32 C/S. The inhibitory capacity of the three TAT-phosphopeptides on dephosphorylation of the pY876 site on the full length GluA2 (GluA2-FL) by the catalytic active STEP32WT was evaluated. Therefore, HEK293 cells were transfected with a pCMV-SPORT6-GRIA2 mammalian expression vector containing the cDNA of full length GluA2 (GluA2-FL). GluA2-FL was immunoprecipitated from cell lysates with anti-GluA2 and tyrosine phosphorylated (phosphorylation proved with anti-pY876). Next, immunoprecipitated GluA2 was treated with a) STEP32 WT, b) STEP32 WT incubated with 0.1 mM TAT-phosphopeptides (TAT-p3Y, TAT-p3Y-sh3, respectively TAT-p-fin 4), c) STEP incubated with 1 mM TAT-phosphopeptides. A sample consisting of immunoprecipitated GluA2 FL untreated with either STEP32 or peptides was also included into the study, as a control. Subsequent WB results showed that all phosphopeptides prevent pY876 of GluA2-FL dephosphorylation by STEP32 WT. TAT-p-fin 4 displayed the highest inhibition of GluA2 dephosphorylation. FIGS. 2D and 2E P show that inhibition of pY876 dephosphorylation by 1 mM p-fin 4 was statistically significant with unpaired t-test with Welch's correction (P<0.05)

Example 7—Immobilization of GST-GluA2 and Peptides on Sensor Chips

Surface plasmon resonance (SPR) experiments were performed using a Biacore 3000 instrument (GE Healthcare™) equipped with CMD500L sensor chips (XanTec Bioanalytics™ GmbH).

Prior to immobilization of peptides, the sensor chip surface was conditioned by injecting a solution consisting of 10 mM sodium tetraborate, 1M NaCl, pH 9.0, for 3 min at a flow rate of 20 µl/min. Then, the sensor surface was activated by injection of a 1:1 mixture of 50 mM NHS (N-hydroxysuccinimide) and 200 mM EDC (1-Ethyl-3-[3-dimethylaminopropyl]carbodiimide hydrochloride) solutions from Amine Coupling Kit (GE Healthcare™), for 15 min at a flow rate of 5 µl/min. The peptides p3Ysh-1, -3, -4, -5, -7, p3Y, p3Y-F2Pmp, 3Ysh-3-F2Pmp and p-fin 4 were dissolved in 10 mM sodium acetate pH 4.0 to reach a concentration of 4-5 mg/ml. The remaining two peptides (p3Y-2 and -6) were first dissolved in 1% ammonium solution and then diluted in 10 mM sodium acetate pH 4.0 to 4-5 mg/ml. Next, each of the diluted peptides were injected on the activated surface of one flow cell at 3-5 µl/min flow rate until the response was between 600 and 1000 RU. The first flow cell of each sensor chip was kept without peptide immobilization as a reference for background subtraction. For most cases, to get an optimal immobilization response, it was necessary to perform successive injections of highly concentrated peptide. Deactivation of the unoccupied activated binding sites on the sensor was performed by injection of a solution of 1M ethanolamine-HCl, pH 8.5, for 13 min at 3 µl/min flow rate. All covalent immobilization steps have been performed at 25° C. using degassed Milli-Q™ deionized water as a running buffer. After surface deactivation with ethanolamine, the immobilization level of each phosphopeptide was estimated from the sensorgrams and the results in terms of response units (RU) are shown in Table 2.

Example 8—Measurement of Binding Kinetics by SPR

These experiments were carried out in order to quantify the strength of the bond between phosphorylated or phosphonomimetic peptides and an inactive mutant of STEP. For the interaction experiments, the immobilized peptides were used as ligands, while the inactive mutant C/S of STEP32 enzyme (>90% purity) was used as the analyte. For each kinetic experiment, at least five different protein concentrations ranging between 100 nM and 500 µM were used. The concentrations of STEP32 C/S were estimated using Pierce™ 660 nm Protein Assay Reagent (Thermo) and a microplate reader. In each kinetic experiment, 50 µl of STEP32 were injected at a flow rate of 10 µl/min using KINJECT command. The association and dissociation time was set to 5 min. After each interaction test, 2-4 cycles of regeneration were performed by injecting 1M NaCl in HBS-EP buffer (0.01 M HEPES pH 7.4, 0.15 M NaCl, 3 mM EDTA, 0.005% v/v Surfactant P20) for 2 min at a flow rate of 20 µl/min. HBS-EP buffer was used as a running buffer. All measurements were carried out at 25° C. The data obtained was processed with BIAevaluation 3.1 software using 1:1 Langmuir fitting model with drifting baseline (using "Kinetics Simultaneous Kd/Ka" module). Nonspecific signals were removed by subtraction of signals from the reference area. Representative sensorgrams are shown in FIGS. 4B, 5A, and 7 and dissociation constant values for the interactions are to be found in Table 2, Table S3 and Table 4.

Example 9—Fluorescence Polarization

In order to differentiate the capacity of the peptides to bind to STEP, a setup to determine the inhibition constant Ki was used based on fluorescence polarization. A fluorescent peptide coupled with 5-carboxytetramethylrhodamine (TAMRA) was used for measuring fluorescence polarization. Phosphonodifluoromethyl alanine was used instead of a tyrosine. The peptide was denominated TAMRA-3Y-F2Pmp (see FIG. 4A) and was ordered from Kinexus™ (Canada). TAMRA-3Y-F$_2$Pmp was dissolved in DMSO to yield a 1 µg/pµl solution. The STEP32 C/S and TAMRA-3Y-F$_2$Pmp concentrations used were 1000 nM and 200 nM, respectively. Inhibitor concentrations were in the range: 0-3 mM. Fluorescence polarization was studied on a Molecular Devices™ SpectraMax™ Paradigm microplate reader with a A41582 type Fluorescence Polarization Cartridge with excitation and emission preset at 535 nm and 595 nm, respectively. For all experiments a 50 mM HEPES, 500 mM NaCl, pH=7.4 buffer was used. Interaction mixtures were equilibrated at 4° C. for 30 min. Plates were centrifuged at 1500 rpm for 10 min. Black NBS 384-well fluorescence plate (Corning™ Cat. No. 3821) and Black NBS 96-well plate, low volume, flat bottom (Thermo™ Cat. No. 237105) were used. Dissociation constant Kd and inhibition constants K for the inhibitor peptides used were determined using a method by Wang [52]. Ki values are to be found in Tables 1-3 and some representative dose-response curves are shown in FIG. 6A.

Example 10—Molecular Modeling

For preparing the protein structures, Schrödinger's Protein Preparation Wizard™ was used. The preparatory steps entailed assigning bond orders and hydrogen bonds, modeling missing loops and sidechains, generating protonation states at a pH of 7.4, optimizing H-bond geometries and running a restrained minimization of the structures [53], [54]. Conformational ensembles for the peptides were generated by a conformational search with mixed torsional and low-mode sampling with Macromodel™, with an energy window of 50 kJ/mol and a maximum atom deviation cutoff of 0.5 Å (to filter out redundant structures) [55]. The conformational ensembles were docked to the binding surface of STEP (PDB structure: 2CJZ [35]) with the rigid docking mode of Glide™ [56], [57]. Sidechain OH and SH groups around the binding site were allowed to rotate (specifically: S397, Y406, S598, C633, Y634, C635, Y678 and S738). Images included in the manuscript were prepared with PyMol™ and Maestro™ [59].

Example 11—Disruption of the BRAG2-GluA2 Complex Using the 3Y Peptide (ATYKEGYNVYG (SEQ ID NO: 73))

Samples containing GST-GluA2 (150 µg) and BRAG2 (60 µg) were bound to Sepharose glutathione beads (20 µl). Prior to binding, the beads were washed thoroughly with interaction buffer (25 mM HEPES, 150 mM NaCl, 1 mM MgCl2, 1% Triton™ X-100, 1 mM DTT, pH=7.5). Triton™ X-100 was used to avoid nonspecific binding and to minimize the risk of protein precipitation. In a subsequent step, 3Y at different concentrations was added to the samples (1000 µM, 100 µM, 10 µM, 1 µM, 0.1 µM). A 2.5 mM solution (0.1 M PBS pH=7.4) was obtained. After incubating the samples for 90 minutes at 4° C. with stirring, the beads were washed with a buffer containing less Triton X-100 (25 mM HEPES, 150 mM NaCl, 1 mM MgCl$_2$, 0.1% Triton™ X-100.1 mM DTT, pH=7.5). The species which remained trapped by the beads were analyzed by SDS-PAGE (FIG. 16). These results clearly show that 3Y (in the range of concentrations 10 µM-1 mM) successfully disrupts the BRAG2-GluA2 complex.

Example 12—Disruption of the BRAG2-GluA2 Complex Using the 3Y, TAT-3Y and 3Y-sh3 Peptides Having the dose dependent quality of 3Y to disrupt the GluA2-BRAG2 complex demonstrated as shown in Example 11, it was further investigated whether this effect was also to be observed with the TAT-coupled 3Y peptide and with the (uncoupled) novel 3Y-sh3 peptide. The results shown in FIG. 17 show that the TAT moiety has no influence on the inhibitory strength of the peptide, but also confirms that the 3Y-sh3 peptide also has a significant disrupting effect on the GST-GluA2-BRAG2 complex.

Pharmacological Tests

Animal Preparation and Drug Administration

At the beginning of the experiment, there have been selected 30 adult male rats (Cantacuzino Institute™, Romania) having an average weight of 350 g (±10 g) and four months old. The animals were housed in the animal unit under controlled conditions of light (a 12-h cycle starting at 07:00 h) and temperature (22° C.). Food and water were provided ad libitum throughout the experiment. Rats were randomly divided into 6 groups (n=5 animals/group) as follows: Control group (sham-operated), Scopolamine (Sco) group (sham-operated, Sco: 0.7 mg/kg b.w., i.p., Sigma-Aldrich™, Darmstadt, Germany), and groups treated with TAT-p3Y, TAT-3Y, TAT-p3Ysh3, and TAT-pfin4 (15 µM, GenScript™) received scopolamine. The doses of the peptides were chosen according to a previous report [60]. Scopolamine hydrobromide (Sco, 0.7 mg/kg) was administered 30 min before behavioral in vivo approaches. Also, the inventors confirm that n=5 animals/group is appropriate using InVivoStat™, and R-based statistical package [61]. Based on a significance level of 0.05, the power to detect a biologically relevant change is 93%.

Peptide Injection Procedure

All surgical procedures were conducted under aseptic conditions, under sodium pentobarbital (50 mg/kg b.w., i.p., Sigma-Aldrich™, Darmstadt, Germany) anesthesia. Rats were mounted in the stereotaxic apparatus with the nose oriented 11° below horizontal zero plane. Two plastic guide cannulas (Portex™, 0.9 mm outer diameter) were bilaterally implanted stereotaxically in the dorsal hippocampus according to the following coordinates: A/P=3.6 mm, M/L=3.1 mm and D/V=2.4 mm. The cannulas were positioned with dental cement (Adhesor™ SpofaDental™) and secured by three stainless steel screw implanted into the skull. After surgery, the rats were isolated in separate cages and protected with a large spectrum antibiotic. Animals were given two weeks to recover from surgery and were handled daily during this period.

The peptides, such as TAT-p3Y and TAT-3Y, were dissolved into dimethyl sulfoxide (DMSO) along with TAT-p3Ysh3 and TAT-pfin4, which were dissolved in saline solution and were infused bilaterally into the dorsal hippocampus at a flow rate of 0.25 µL/min during 4 min by a Hamilton syringe (5 µL). The concentration of peptides was 15 µM, and the volume of infusion was 1 µL. Before withdrawal, the syringe was left in place for an additional 90 min to minimize dragging the injected solution. The sham-operated rats were injected with sterile saline. The location of the cannulas in the brain was verified by injecting a dye (trypan blue) through each cannula at the end of the experiment.

Behavioral Assays

Y-Maze Test

Spontaneous alternation behavior was evaluated in a single-session Y-maze, as previously described by Jackson Postu et al [63]. In the present study, the Y-maze used was built of Plexiglas having the following dimensions: 25 cm high, 35 cm long, 10 cm wide for each arm, and a central area in an equilateral triangular shape. Each rat was positioned at the end of one arm and given the possibility to move for 8 min. The percentage of the involuntary alternation was determined according to the formula:

(number of alternation/total entries−2)×100.

Radial Arm-Maze Test

As described before by Olton and Samuelson and Postu et al [63], using a radial arm maze test (RAM), the spatial memory was determined for one week.

The maze comprised eight arms marked from 1 to 8 (48 cm×12 cm), with a radial extension of 32 cm in diameter from the central area, and it had 50 mg food pellets at the end of arms 1, 2, 4, 5, and 7. Four days of habituation sessions were performed. Rats were instructed to move to the end of the arms and to eat the bait during 5 min sessions. After habituation, only one trial per day was granted to all rats. For working and reference memory tasks, each rat was individually placed in the center of the maze. Determinations have been carried out by (i) assessing the number of working memory errors (getting inside an arm that contains food, but earlier stepped into) and (ii) calculating the number of reference memory errors (calculating animal entries in an arm without food).

Elevated Plus-Maze Test

Behavior in the elevated plus-maze test (E.P.M.) is utilized to assess exploration, anxiety and motor behavior. Each rat was placed in the center of the maze facing one closed arm. Behavior was observed for 5 min, and the time spent and the number of entries into the open arms were counted [65]. The percentages of time spent in the open arms were calculated using the formula:

(time spent in the open arms/time spent in all arms)×100.

Forced Swimming Test

The forced swimming test (F.S.T.) is used for assessing depressive-like responses [66]. The depressive-like response was assessed, basically using the same method described by Campos et al. [67], but with modifications. On the first day of the experiments (pretest session), rats were individually placed into cylindrical recipients (diameter 30 cm, height 59 cm) containing 25 cm of water at 26±1° C. The animals were left to swim for 15 min before being removed, dried with heated towels, and returned to their cages. The procedure was repeated 24 h later, in a 6 min swim session (test session). During the test session, the following behavioral responses were recorded: (i) immobility (time spent floating with the minimal movements to keep the head above the water); and (ii) swimming (time spent with active swimming movements).

Statistical Analyses

Data are expressed as mean±S.E.M and were statistically analyzed by one-way analysis of variance (ANOVA) followed by Tukey's HSD post-hoc test for comparison between multiple groups, considering treatment as a factor. All analyses were performed by GraphPad™ 8.0 software, and the significance was set at p<0.05. Correlation between the behavioral scores in different tasks was estimated by the Pearson correlation coefficient (r).

From the description of the invention set forth in detail in connection with its multiple embodiments and combinations thereof, a skilled person will understand and appreciate that some modifications may be made to suit a particular situation without departing from the teachings of the invention. These modifications may be made in the spirit of the invention and within the limits conferred by the scope of protection as defined in the claims.

Amino acid sequence of STEP32 C/S variant of STEP phosphatase:

```
                                              (SEQ ID NO: 7)
SMSRVLQAEELHEKALDPFLLQAEFFEIPMNFVDPK

EYDIPGLVRKNRYKTILPNPHSRVCLTSPDPDDPL

SSYINANYIRGYGGEEKVYIATQGPIVSTVADFWR

MVWQEHTPIIVMITNIEEMNEKCTEYWPEEQVAYD
```

```
-continued
GVEITVQKVIHTEDYRLRLISLKSGTEERGLKHYW

FTSWPDQKTPDRAPPLLHLVREVEEAAQQEGPHCA

PIIVHSSAGIGRTGCFIATSICCQQLRQEGVVDIL

KTTCQLRQDRGGMIQTCEQYQFVHHVMSLYEKQLS

HQS
```

BIBLIOGRAPHY

References

[1] J. R. Whitlock, A. J. Heynen, M. G. Shuler, and M. F. Bear, "Learning induces long-term potentiation in the hippocampus," Science (80-.)., vol. 313, no. 5790, pp. 1093-1097, 2006, doi: 10.1126/science.1128134.

[2] S. Guntupalli, J. Widagdo, and V. Anggono, "Amyloid-β-Induced Dysregulation of AMPA Receptor Trafficking," Neural Plasticity, vol. 2016. Hindawi Limited, 2016, doi: 10.1155/2016/3204519.

[3] P. Temkin, W. Morishita, D. Goswami, K. Arendt, L. Chen, and R. Malenka, "The Retromer Supports AMPA Receptor Trafficking During LTP," Neuron, vol. 94, no. 1, pp. 74-82.e5, April 2017, doi: 10.1016/j.neuron.2017.03.020.

[4] S. S. Jang et al., "Regulation of STEP61 and tyrosine-phosphorylation of NMDA and AMPA receptors during homeostatic synaptic plasticity," Mol. Brain, vol. 8, no. 1, pp. 1-8, 2015, doi: 10.1186/s13041-015-0148-4.

[5] R. Scholz, S. Berberich, L. Rathgeber, A. Kolleker, G. Kohr, and H. C. Kornau, "AMPA Receptor Signaling through BRAG2 and Arf6 Critical for Long-Term Synaptic Depression," Neuron, vol. 66, no. 5, pp. 768-780, 2010, doi: 10.1016/j.neuron.2010.05.003.

[6] T. D. Gould, C. A. Zarate, and S. M. Thompson, "Molecular Pharmacology and Neurobiology of Rapid-Acting Antidepressants," Annu. Rev. Pharmacol. Toxicol., vol. 59, no. 1, pp. 213-236, 2019, doi: 10.1146/annurev-pharmtox-010617-052811.

[7] M. R. Witten et al., "X-ray Characterization and Structure-Based Optimization of Striatal-Enriched Protein Tyrosine Phosphatase Inhibitors," J. Med. Chem., vol. 60, no. 22, pp. 9299-9319, November 2017, doi: 10.1021/acs.jmedchem.7b01292.

[8] F. Pilato et al., "Synaptic plasticity in neurodegenerative diseases evaluated and modulated by in vivo neurophysiological techniques," Mol. Neurobiol., vol. 46, no. 3, pp. 563-571, 2012, doi: 10.1007/s12035-012-8302-9.

[9] T. Takeuchi, A. J. Duszkiewicz, and R. G. M. Morris, "The synaptic plasticity and memory hypothesis: Encoding, storage and persistence," Philos. Trans. R. Soc. B Biol. Sci., vol. 369, no. 1633, 2014, doi: 10.1098/rstb.2013.0288.

[10] G. L. Collingridge, S. Peineau, J. G. Howland, and Y. T. Wang, "Long-term depression in the CNS," Nat. Rev. Neurosci., vol. 11, no. 7, pp. 459-473, July 2010, doi: 10.1038/nrn2867.

[11] S. H. Shi et al., "Rapid spine delivery and redistribution of AMPA receptors after synaptic NMDA receptor activation.," Science, vol. 284, no. 5421, pp. 1811-6, June 1999, doi: 10.1126/science.284.5421.1811.

[12] R. C. Carroll, D. V. Lissin, M. Von Zastrow, R. A. Nicoll, and R. C. Malenka, "Rapid redistribution of glutamate receptors contributes to long-term depression in hippocampal cultures," Nat. Neurosci., vol. 2, no. 5, pp. 454-460, 1999, doi: 10.1038/8123.

[13] M. Park, "AMPA receptor trafficking for postsynaptic potentiation," Front. Cell. Neurosci., vol. 12, no. Oct., pp. 1-10, 2018, doi: 10.3389/fncel.2018.00361.

[14] J. D. Shepherd and R. L. Huganir, "The Cell Biology of Synaptic Plasticity: AMPA Receptor Trafficking," Annu. Rev. Cell Dev. Biol., vol. 23, no. 1, pp. 613-643, November 2007, doi: 10.1146/annurev.cellbio.23.090506.123516.

[15] W. Lu et al., "Subunit Composition of Synaptic AMPA Receptors Revealed by a Single-Cell Genetic Approach," Neuron, vol. 62, no. 2, pp. 254-268, April 2009, doi: 10.1016/J.NEURON.2009.02.027.

[16] T. E. Chater and Y. Goda, "The role of AMPA receptors in postsynaptic mechanisms of synaptic plasticity," Front. Cell. Neurosci., vol. 8, no. November, pp. 1-14, 2014, doi: 10.3389/fncel.2014.00401.

[17] G. H. Diering and R. L. Huganir, "The AMPA Receptor Code of Synaptic Plasticity," Neuron, vol. 100, no. 2, pp. 314-329, 2018, doi: 10.1016/j.neuron.2018.10.018.

[18] J. M. Henley and K. A. Wilkinson, "AMPA receptor trafficking and the mechanisms underlying synaptic plasticity and cognitive aging," Dialogues Clin. Neurosci., vol. 15, no. 1, pp. 11-27, 2013.

[19] G. Ahmadian et al., "Tyrosine phosphorylation of GluR2 is required for insulin-stimulated AMPA receptor endocytosis and LTD," EMBO J., vol. 23, no. 5, pp. 1040-1050, March 2004, doi: 10.1038/sj.emboj.7600126.

[20] T. Hayashi and R. L. Huganir, "Tyrosine Phosphorylation and Regulation of the AMPA Receptor by Src Family Tyrosine Kinases," J. Neurosci., vol. 24, no. 27, pp. 6152-6160, 2004, doi: 10.1523/JNEUROSCI.0799-04.2004.

[21] P. R. Moult et al., "Tyrosine phosphatases regulate AMPA receptor trafficking during metabotropic glutamate receptor-mediated long-term depression," J. Neurosci., vol. 26, no. 9, pp. 2544-2554, 2006, doi: 10.1523/JNEUROSCI.4322-05.2006.

[22] P. W. Tak et al., "Hippocampal long-term depression mediates acute stress-induced spatial memory retrieval impairment," Proc. Natl. Acad. Sci. U.S.A, vol. 104, no. 27, pp. 11471-11476, 2007, doi: 10.1073/pnas.0702308104.

[23] K. Brebner et al., "Neuroscience: Nucleus accumbens long-term depression and the expression of behavioral sensitization," Science (80-.)., vol. 310, no. 5752, pp. 1340-1343, 2005, doi: 10.1126/science.1116894.

[24] C. J. Fox, K. Russell, A. K. Titterness, Y. T. Wang, and B. R. Christie, "Tyrosine phosphorylation of the GluR2 subunit is required for long-term depression of synaptic efficacy in young animals in vivo.," Hippocampus, vol. 17, no. 8, pp. 600-605, 2007, doi: 10.1002/hipo.20302.

[25] M. C. Van den Oever et al., "Prefrontal cortex AMPA receptor plasticity is crucial for cue-induced relapse to heroin-seeking.," Nat. Neurosci., vol. 11, no. 9, pp. 1053-1058, September 2008, doi: 10.1038/nn.2165.

[26] S. Y. Yu, D. C. Wu, L. Liu, Y. Ge, and Y. T. Wang, "Role of AMPA receptor trafficking in NMDA receptor-dependent synaptic plasticity in the rat lateral amygdala.," J. Neurochem., vol. 106, no. 2, pp. 889-899, July 2008, doi: 10.1111/j.1471-4159.2008.05461.x.

[27] K. Kohda, W. Kakegawa, S. Matsuda, T. Yamamoto, H. Hirano, and M. Yuzaki, "The δ2 glutamate receptor gates long-term depression by coordinating interactions between two AMPA receptor phosphorylation sites.,"

[28] Y. Zhang et al., "The tyrosine phosphatase STEP mediates AMPA receptor endocytosis after metabotropic glutamate receptor stimulation.," *J. Neurosci.*, vol. 28, no. 42, pp. 10561-6, October 2008, doi: 10.1523/JNEUROSCI.2666-08.2008.

[29] V. Anggono and R. L. Huganir, "Regulation of AMPA receptor trafficking and synaptic plasticity," *Curr. Opin. Neurobiol.*, vol. 22, no. 3, pp. 461-469, June 2012, doi: 10.1016/J.CONB.2011.12.006.

[30] Y. Zhang et al., "Genetic reduction of striatal-enriched tyrosine phosphatase (STEP) reverses cognitive and cellular deficits in an Alzheimer's disease mouse model.," *Proc. Natl. Acad. Sci. U.S.A*, vol. 107, no. 44, pp. 19014-9, November 2010, doi: 10.1073/pnas.1013543107.

[31] Y. Zhao, S. Chen, C. Yoshioka, I. Baconguis, and E. Gouaux, "Architecture of fully occupied GluA2 AMPA receptor-TARP complex elucidated by cryo-EM.," *Nature*, vol. 536, no. 7614, pp. 108-11, July 2016, doi: 10.1038/nature18961.

[32] S. F. Altschul, W. Gish, W. Miller, E. W. Myers, and D. J. Lipman, "Basic local alignment search tool," *J. Mol. Biol.*, vol. 215, no. 3, pp. 403-410, 1990, doi: 10.1016/S0022-2836(05)80360-2.

[33] "BLAST: Basic Local Alignment Search Tool.".

[34] J. Xu et al., "Extrasynaptic NMDA receptors couple preferentially to excitotoxicity via calpain-mediated cleavage of STEP," *J. Neurosci.*, vol. 29, no. 29, pp. 9330-9343, 2009, doi: 10.1523/JNEUROSCI.2212-09.2009.

[35] J. Eswaran et al., "Crystal structures and inhibitor identification for PTPN5, PTPRR and PTPN7: A family of human MAPK-specific protein tyrosine phosphatases," *Biochem. J.*, vol. 395, no. 3, pp. 483-491, 2006, doi: 10.1042/BJ20051931.

[36] A. J. Barr et al., "Large-Scale Structural Analysis of the Classical Human Protein Tyrosine Phosphatome," *Cell*, vol. 136, no. 2, pp. 352-363, 2009, doi: 10.1016/j.cell.2008.11.038.

[37] A. L. Hopkins, G. M. Keseru, P. D. Leeson, D. C. Rees, and C. H. Reynolds, "The role of ligand efficiency metrics in drug discovery," *Nat. Rev. Drug Discov.*, vol. 13, no. 2, pp. 105-121, 2014, doi: 10.1038/nrd4163.

[38] K. S. Tang, "The cellular and molecular processes associated with scopolamine-induced memory deficit: A model of Alzheimer's biomarkers," *Life Sci.*, vol. 233, no. Jul., p. 116695, 2019, doi: 10.1016/j.lfs.2019.116695.

[39] D. K. Doguc, N. Delibas, H. Vural, I. Altuntas, R. Sutcu, and Y. Sonmez, "Effects of chronic scopolamine administration on spatial working memory and hippocampal receptors related to learning," *Behav. Pharmacol.*, vol. 23, no. 8, pp. 762-770, 2012, doi: 10.1097/FBP.0b013e32835a38af.

[40] H. B. Kim et al., "ESP-102, a Combined Herbal Extract of Angelica gigas, Saururus chinensis, and Schisandra chinensis, Changes Synaptic Plasticity and Attenuates Scopolamine-Induced Memory Impairment in Rat Hippocampus Tissue," *Evidence-based Complement. Altern. Med.*, vol. 2016, pp. 1-9, 2016, doi: 10.1155/2016/8793095.

[41] E. S. Hwang et al., "Acute rosmarinic acid treatment enhances long-term potentiation, BDNF and GluR-2 protein expression, and cell survival rate against scopolamine challenge in rat organotypic hippocampal slice cultures," *Biochem. Biophys. Res. Commun.*, vol. 475, no. 1, pp. 44-50, 2016, doi: 10.1016/j.bbrc.2016.04.153.

[42] D. R. Shimshek et al., "Forebrain-specific glutamate receptor B deletion impairs spatial memory but not hippocampal field long-term potentiation," *J. Neurosci.*, vol. 26, no. 33, pp. 8428-8440, 2006, doi: 10.1523/JNEUROSCI.5410-05.2006.

[43] D. V Venkitaramani, P. J. Moura, M. R. Picciotto, and P. J. Lombroso, "Striatal-enriched protein tyrosine phosphatase (STEP) knockout mice have enhanced hippocampal memory.," *Eur. J. Neurosci.*, vol. 33, no. 12, pp. 2288-2298, June 2011, doi: 10.1111/j.1460-9568.2011.07687.x.

[44] U. Falter, A. Gower, and J. Gobert, "Anxiogenic Effects of Scopolamine Observed in Rats in the Elevated Plus-maze BT—New Concepts in Anxiety," M. Briley and S. E. File, Eds. London: Macmillan Education UK, 1991, pp. 332-337.

[45] S. Lee et al., "Sulforaphane alleviates scopolamine-induced memory impairment in mice," *Pharmacol. Res.*, vol. 85, pp. 23-32, 2014, doi: 10.1016/j.phrs.2014.05.003.

[46] J. W. Smythe, S. Bhatnagar, D. Murphy, and C. Timothy, "The Effects of Intrahippocampal Scopolamine Infusions on Anxiety in Rats as Measured by the Black—White Box Test," vol. 45, no. 1, pp. 89-93, 1998.

[47] M. J. Stillman, B. Shukitt-Hale, B. P. Coffey, A. Levy, and H. R. Lieberman, "In Vivo Hippocampal Acetylcholine Release During Exposure to Acute Stress.," *Stress*, vol. 1, no. 4, pp. 191-200, August 1997, doi: 10.3109/10253899709013740.

[48] L. Pavlovsky, Y. Bitan, H. Shalev, Y. Serlin, and A. Friedman, "Stress-induced altered cholinergic—glutamatergic interactions in the mouse hippocampus," *Brain Res.*, vol. 1472, pp. 99-106, 2012, doi: 10.1016/j.brainres.2012.05.057.

[49] G. Whitehead et al., "Acute stress causes rapid synaptic insertion of Ca2+-permeable AMPA receptors to facilitate long-term potentiation in the hippocampus.," *Brain*, vol. 136, no. Pt 12, pp. 3753-3765, 2013, doi: 10.1093/brain/awt293.

[50] M. Wang, V. S. Ramasamy, M. Samidurai, and J. Jo, "Acute restraint stress reverses impaired LTP in the hippocampal CA1 region in mouse models of Alzheimer's disease," *Sci. Rep.*, vol. 9, no. 1, pp. 1-9, 2019, doi: 10.1038/s41598-019-47452-6.

[51] K. Martinowich et al., "Roles of p75(NTR), long-term depression, and cholinergic transmission in anxiety and acute stress coping.," *Biol. Psychiatry*, vol. 71, no. 1, pp. 75-83, January 2012, doi: 10.1016/j.biopsych.2011.08.014.

[52] Z. X. Wang, "An exact mathematical expression for describing competitive binding of two different ligands to a protein molecule.," *FEBS Lett.*, vol. 360, no. 2, pp. 111-114, February 1995, doi: 10.1016/0014-5793(95)00062-e.

[53] "Schrödinger Release 2017-4: Schrödinger Suite 2017-4 Protein Preparation Wizard; Epik, Schrödinger, LLC, New York, NY, 2017; Impact, Schrödinger, LLC, New York, NY, 2017; Prime, Schrödinger, LLC, New York, NY, 2017.".

[54] G. M. Sastry, M. Adzhigirey, T. Day, R. Annabhimoju, and W. Sherman, "Protein and ligand preparation: parameters, protocols, and influence on virtual screening enrichments.," *J. Comput. Aided Mol. Des.*, vol. 27, no. 3, pp. 221-34, March 2013, doi: 10.1007/s10822-013-9644-8.

"Schrödinger Release 2017-4: Macromodel, Schrödinger, LLC, New York, NY, 2017.".

[56] R. A. Friesner et al., "Glide: a new approach for rapid, accurate docking and scoring. 1. Method and assessment of docking accuracy," *J. Med Chem.*, vol. 47, no. 7, pp. 1739-1749, 2004.

[57] T. A. Halgren et al., "Glide: a new approach for rapid, accurate docking and scoring. 2. Enrichment factors in database screening," *J. Med Chem.*, vol. 47, no. 7, pp. 1750-1759, 2004.

[58] "The PyMOL Molecular Graphics System, Version 1.7.7.1 Schrödinger, LLC.".

[59] "Schrödinger Release 2017-4: Maestro, Schrödinger, LLC, New York, NY, 2017.".

[60] P. V. Migues, O. Hardt, P. Finnie, Y. W. Wang, and K. Nader, "The maintenance of long-term memory in the hippocampus depends on the interaction between N-ethylmaleimide-sensitive factor and GluA2.," *Hippocampus*, vol. 24, no. 9, pp. 1112-1119, September 2014, doi: 10.1002/hipo.22295.

[61] S. T. Bate and R. A. Clark, *The Design and Statistical Analysis of Animal Experiments*. Cambridge: Cambridge University Press, 2014.

[62] L. L. Jackson, "VTE on an elevated T-maze.," *J. Comp. Psychol.*, vol. 36, no. 2, pp. 99-107, 1943, doi: 10.1037/h0058536.

[63] P. A. Postu et al., "*Pinus halepensis* essential oil attenuates the toxic Alzheimer's amyloid beta (1-42)-induced memory impairment and oxidative stress in the rat hippocampus.," *Biomed Pharmacother.*, vol. 112, p. 108673, April 2019, doi: 10.1016/j.biopha.2019.108673.

[64] D. S. Olton and R. J. Samuelson, "Remembrance of places passed: Spatial memory in rats," *J. Exp. Psychol. Anim. Behav. Process.*, 1976, doi: 10.1037/0097-7403.2.2.97.

[65] Y. Hayashi, S. Sogabe, Y. Hattori, and J. Tanaka, "Anxiolytic and hypnotic effects in mice of roasted coffee bean volatile compounds," *Neurosci. Lett.*, 2012, doi: 10.1016/j.neulet.2012.10.044.

[66] J. F. Cryan, A. Markou, and I. Lucki, "Assessing antidepressant activity in rodents: Recent developments and future needs," *Trends in Pharmacological Sciences*. 2002, doi: 10.1016/S0165-6147(02)02017-5.

[67] M. M. Campos, E. S. Fernandes, J. Ferreira, A. R. S. Santos, and J. B. Calixto, "Antidepressant-like effects of Trichilia catigua (Catuaba) extract: evidence for dopaminergic-mediated mechanisms.," *Psychopharmacology* (Berl)., vol. 182, no. 1, pp. 45-53, October 2005, doi: 10.1007/s00213-005-0052-1.

---

The invention claimed is:

1. A synthetic peptide consisting of the amino acid sequence of E-G-Y-N-V-Xa1-E (SEQ ID NO: 77), wherein Xa1 is a phosphorylated tyrosine (Y) or 4-(phosphonodifluoromethyl)-L-phenylalanine (F2Pmp).

2. The synthetic peptide of claim 1, wherein the Xa1 is a phosphorylated Y.

3. The synthetic peptide of claim 1, wherein the Xa1 is a 4-(phosphonodifluoromethyl)-L-phenylalanine (F2Pmp).

* * * * *